(12) United States Patent
Slade

(10) Patent No.: US 9,962,477 B2
(45) Date of Patent: May 8, 2018

(54) CARTRIDGE SYSTEMS USEFUL IN CLEANING DIALYSIS SOLUTIONS

(71) Applicant: Fresenius Medical Care Holdings, Inc., Waltham, MA (US)

(72) Inventor: Charles J. Slade, Cambridge, MA (US)

(73) Assignee: Fresenius Medical Care Holdings, Inc., Waltham, MA (US)

(*) Notice: Subject to any disclaimer, the term of this patent is extended or adjusted under 35 U.S.C. 154(b) by 198 days.

(21) Appl. No.: 14/983,942

(22) Filed: Dec. 30, 2015

(65) Prior Publication Data

US 2017/0189598 A1 Jul. 6, 2017

(51) Int. Cl.

| | |
|---|---|
| *A61M 1/16* | (2006.01) |
| *B01D 61/30* | (2006.01) |
| *B01D 15/10* | (2006.01) |
| *B01J 20/20* | (2006.01) |
| *B01J 31/00* | (2006.01) |
| *B01J 39/02* | (2006.01) |
| *B01J 39/12* | (2006.01) |
| *B01J 41/02* | (2006.01) |
| *B01J 41/10* | (2006.01) |
| *B01D 15/14* | (2006.01) |
| *B01J 47/024* | (2017.01) |
| *B01D 24/40* | (2006.01) |

(Continued)

(52) U.S. Cl.
CPC ............ *A61M 1/1696* (2013.01); *B01D 15/10* (2013.01); *B01D 15/14* (2013.01); *B01D 24/40* (2013.01); *B01D 61/30* (2013.01); *B01J 20/043* (2013.01); *B01J 20/20* (2013.01); *B01J 20/28052* (2013.01); *B01J 31/003* (2013.01); *B01J 39/02* (2013.01); *B01J 39/12* (2013.01); *B01J 41/02* (2013.01); *B01J 41/10* (2013.01); *B01J 47/024* (2013.01); *A61M 2206/10* (2013.01); *A61M 2206/18* (2013.01); *A61M 2206/20* (2013.01); *B01J 2220/62* (2013.01); *C02F 2201/006* (2013.01)

(58) Field of Classification Search
None
See application file for complete search history.

(56) References Cited

U.S. PATENT DOCUMENTS

| | | |
|---|---|---|
| 3,669,878 A | 6/1972 | Marantz et al. |
| 3,669,880 A | 6/1972 | Marantz et al. |
| 3,697,410 A | 10/1972 | Johnson et al. |

(Continued)

FOREIGN PATENT DOCUMENTS

| | | |
|---|---|---|
| WO | 2013/028809 A2 | 2/2013 |
| WO | 2015/080895 A1 | 6/2015 |

OTHER PUBLICATIONS

International Search Report and Written Opinion issued in corresponding International Patent Application No. PCT/US2016/066492 dated Mar. 21, 2017 (18 pages).

(Continued)

*Primary Examiner* — Chester T Barry
(74) *Attorney, Agent, or Firm* — Kilyk & Bowersox, P.L.L.C.

(57) ABSTRACT

Sorbent cartridge systems useful in regenerating or purifying dialysis solutions are described as well as methods to regenerate or purify spent dialysis solutions. Dialysis systems using the sorbent cartridge system of the present invention are further described.

17 Claims, 12 Drawing Sheets

(51) Int. Cl.
*B01J 20/04* (2006.01)
*B01J 20/28* (2006.01)

(56) References Cited

U.S. PATENT DOCUMENTS

| | | | |
|---|---|---|---|
| 3,697,418 A | 10/1972 | Johnson et al. | |
| 3,703,959 A | 11/1972 | Raymond | |
| 3,850,835 A | 11/1974 | Marantz et al. | |
| 3,989,622 A | 11/1976 | Marantz et al. | |
| 3,989,625 A | 11/1976 | Mason | |
| 4,025,608 A | 5/1977 | Tawil et al. | |
| 4,213,859 A | 7/1980 | Smakman et al. | |
| 4,256,718 A | 3/1981 | McArthur et al. | |
| 4,360,507 A | 11/1982 | McArthur et al. | |
| 4,460,555 A | 7/1984 | Thompson | |
| 4,484,599 A | 11/1984 | Hanover et al. | |
| 4,495,129 A | 1/1985 | Newberry et al. | |
| 4,558,996 A | 12/1985 | Becker | |
| D282,578 S | 2/1986 | Humphreys et al. | |
| 5,326,036 A | 7/1994 | Wilger | |
| 6,627,164 B1 | 9/2003 | Wong | |
| 6,878,283 B2 | 4/2005 | Thompson | |
| 7,033,498 B2 | 4/2006 | Wong | |
| 8,012,118 B2 | 9/2011 | Curtin et al. | |
| 8,343,346 B2 | 1/2013 | Crnkovich et al. | |
| 8,366,921 B2 | 2/2013 | Beden et al. | |
| 8,475,399 B2 | 7/2013 | Fulkerson | |
| 8,500,994 B2 | 8/2013 | Weaver et al. | |
| 8,580,112 B2 | 11/2013 | Updyke et al. | |
| 8,597,505 B2 | 12/2013 | Fulkerson et al. | |
| 8,663,463 B2 | 3/2014 | Weaver et al. | |
| 9,707,330 B2 * | 7/2017 | Kelly | A61M 1/1696 |
| 2002/0112609 A1 * | 8/2002 | Wong | A61M 1/1696 96/131 |
| 2005/0045232 A1 * | 3/2005 | Van Decker | E03C 1/023 137/561 A |
| 2006/0140840 A1 | 6/2006 | Wong | |
| 2010/0078387 A1 | 4/2010 | Wong | |
| 2011/0203985 A1 | 8/2011 | Reid | |
| 2012/0234762 A1 | 9/2012 | Wong | |
| 2013/0030356 A1 | 1/2013 | Ding et al. | |
| 2013/0199998 A1 * | 8/2013 | Kelly | A61M 1/1696 210/646 |
| 2013/0206706 A1 * | 8/2013 | Ekholm | B01D 29/66 210/797 |
| 2014/0231302 A1 * | 8/2014 | Goyal | A61B 19/026 206/571 |
| 2014/0326671 A1 * | 11/2014 | Kelly | A61M 1/1696 210/662 |
| 2015/0258266 A1 | 9/2015 | Merchant et al. | |

OTHER PUBLICATIONS

"Guide to Custom Dialysis," COBE Renal Care, Product No. 306100-005, Revision E, Sep. 1993, (54 pages).

"Sorbent Dialysis Primer," COBE Renal Care, Product No. 306100-006, Edition 4, Sep. 1993, (56 pages).

* cited by examiner

CARTRIDGE SYSTEMS USEFUL IN CLEANING DIALYSIS SOLUTIONS

BACKGROUND OF THE INVENTION

The present invention relates to cartridge systems such as ion exchange cartridge or adsorption cartridge based systems which are useful, for instance, in dialysis. In particular, the present invention relates in general to the regeneration or purification of used dialysate fluids. The present invention further relates to methods of conducting dialysis using certain cartridge systems.

Dialysis is a treatment that removes the waste products and excess fluid that accumulate in the blood as a result of kidney failure. Chronic renal failure is when the renal function has deteriorated to about 25% of normal. This amount of deterioration causes significant changes in the blood chemistry and is about the time that people feel poorly enough that they seek medical care. Peritoneal dialysis (PD) is one form of dialysis. With this treatment, a mild saltwater solution containing dextrose and electrolytes called dialysate is put into the peritoneal cavity. Because there is a rich blood supply to this abdominal cavity, urea and other toxins from the blood and fluid are moved into the dialysate, thereby cleaning the blood. The dialysate is then drained from the peritoneum. Later "fresh" dialysate is again put into the peritoneum.

Also, there is hemodialysis. This is a method of blood purification in which blood is continually removed from the body during a treatment session and passed through a dialyzer (artificial kidney) where metabolic waste and excess water are removed and pH and acid/base balances are normalized. The blood is simultaneously returned to the body. The dialyzer is a small disposable device consisting of a semi-permeable membrane. The membrane allows the wastes, electrolytes, and water to cross but restricts the passage of large molecular weight proteins and blood cells. Blood is pumped across one side of the membrane as dialysate is pumped in the opposite direction across the other side of the membrane. The dialysate is highly purified water with salts and electrolytes added. The machine is a control unit which acts to pump and control pressures, temperatures, and electrolyte concentrations of the blood and the dialysate. The average length of one hemodialysis treatment is 3-5 hours.

There are several types of hemodialysis:

a) Single Pass—hemodialysis is the most common treatment for renal disease. Most hemodialysis treatments are performed with single pass dialysis machines. They are called single pass because the dialysate (cleaning solution) passes by the blood in the dialyzer one time and then is disposed. Single pass dialysis machines generally require:
1) a water source capable of delivering at least 1000-1500 ml/min (assuming a 50% rejection rate by the reverse osmosis ("R.O.") system)
2) a water purification system sufficient of providing a continuous flow of 500-800 ml/min of purified water.
3) an electrical circuit of at least 15 amps in order to pump and heat 500-800 ml of water/min.
4) a floor drain or any other receptacle capable of accommodating at least 500 ml of used dialysate/minute as well as the rejected water from the R.O. system.

b) Sorbent Dialysis—does not require a continuous water source, a separate water purification machine or a floor drain because it continuously regenerates a small volume of dialysate and incorporates a water treatment system within the machine. Therefore, sorbent systems are more portable.

1) sorbent systems typically require only a 5 amp electrical source because they recycle the same small volume of dialysate throughout the dialysis procedure. The heavy duty dialysate pumps and heaters used for large volumes of dialysate in single pass dialysis are not needed.
2) the sorbent system can use 6-12 liters of tap water from which dialysate is made for an entire treatment.
3) the sorbent system uses a sorbent cartridge—which acts both as a water purifier and as a component to regenerate used dialysate into fresh dialysate. The infusate system acts with it to properly balance the electrolyte composition of the regenerated dialysate.

The sorbent cartridge containing zirconium phosphate (ZrP) and hydrous zirconium oxide (HZO) ion-exchange materials has been historically used for the REDY regeneration hemodialysis system. The scheme of the REDY cartridge is shown in FIG. 1. The sorbent cartridge is shown with the inlet and the outlet identified as numeral 11 and numeral 13, respectively. FIG. 2 shows various functions of each layer in a REDY cartridge.

The principle of the REDY cartridge is based on the hydrolysis of urea to ammonium carbonate by the enzymatic reaction of urease. The following equation shows a reaction for urea conversion to ammonia in the presence of urease:

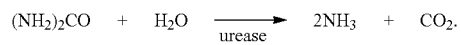

The ammonia and ammonium ions are then removed by the zirconium phosphate in exchange for the hydrogen ions and $Na^+$ ions, which are counter-ions in the cation exchanger. Zirconium phosphate also serves as cation exchanger to remove Ca, Mg, K, and all toxic metals in dialysate, thus allowing a balance of electrolyte level in the patient's blood (Ca, Mg, K) to be maintained by using an infusate system, as well as providing safety for dialysis treatment with regard to water quality. The carbonate from the urea hydrolysis then combines with the hydrogen ions in zirconium phosphate to form bicarbonate, which is delivered to the uremic patient as a base to correct for acidosis. Zirconium phosphate can be represented as inorganic cation exchange material with the molecular structure as shown below:

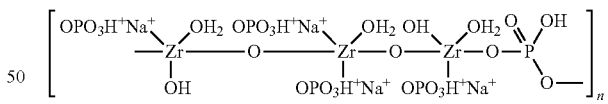

As shown, the material contains both $H^+$ and $Na^+$ as counter-ions, which are responsible for ion exchange. The relative content of these ions can be controlled by the pH to which acid ZrP (or $H^+ZrP$) is titrated with NaOH. The composition of the resultant product of titration, $Na_x^+H_{2-x}^+ZrP$ (or abbreviated as "NaHZrP" herein), may vary during ion exchange processes in dialysate. The hydrous zirconium oxide (HZO) containing acetate (HZO.Ac) as a counter ion serves as an anion exchanger to remove phosphate. The material also prevents leaching of phosphate from NaHZrP and removes toxic anions (e.g., fluoride) in water that may cause harm to a patient during dialysis. The acetate released during ion exchange is also a base to correct for acidosis by acetate metabolism. The compositional formula of hydrous zirconium oxide (HZO) can be $ZrO_2 \cdot nH_2O$ (i.e. zirconium oxide hydrate) or $ZrO_2.nOH \ldots H^+An^-$ in the anion form wherein $An^-$ is an anion attached to HZO, such as acetate ("Ac"), chloride, etc. Without the anion, it can be considered as partially oxalated zirconium hydroxide with various degrees of $O^{2-}$, $OH^-$ and $H_2O$ bonded to Zr, i.e., $Zr(OH)_xO_y(H_2O)_z$. The granular activated carbon in the cartridge is used in the REDY cartridge for the removal of creatinine, uric acid, and nitrogenous metabolic waste of the patient as well as chlorine and chloramine from water.

As indicated, a sorbent cartridge usually includes multiple layers that comprise a similar or substantially chemical composition in each given layer. Flow distribution in a given cartridge layer of the sorbent cartridge can vary across the layer. Channeling phenomenon can occur in a peripheral region of a cartridge layer or layers of a cartridge that are located nearer to the cartridge wall. Fluid flow can increase in the peripheral region of a layer or layers at the expense of a central region thereof located further from the cartridge wall. This is undesirable as it can result in separate regions of overly-used material and unused (or underused) material in the same layer of the cartridge. This can lead to inefficient treatment performance, early or premature exhaustion of a cartridge component, shortening of the useful life of cartridge, unused material in the spent cartridge, or combinations of these problems. Sorbent cartridge designs would be preferred that can further reduce or prevent variations in flow distribution from occurring in the sorbent cartridge. Accordingly, in the area of dialysis, it would be beneficial to overcome one or more of the above-described disadvantages.

SUMMARY OF THE PRESENT INVENTION

A feature of the present invention is to provide cartridge system configurations having improved flow distribution in the cartridges, which are useful in the regeneration or purification of solutions, such as solutions containing waste products and/or impurities.

A further feature of the present invention is to provide cartridge system configurations with more uniform flow distribution in the cartridges, which are useful in the regeneration or purification of dialysis solutions such as hemodialysis or peritoneal dialysis solutions or other dialysate solutions.

A further feature of the present invention is to provide a sorbent cartridge system for regenerating or purifying spent dialysis fluid which can reduce non-uniform flow distribution in dialysate fluids flowing through one or more solid particulate layers of the sorbent cartridge.

A further feature of the present invention is to provide methods to regenerate or purify spent dialysis fluids which can use such sorbent cartridge systems such as to improve the performance efficiency and reduce the amount of unused cartridge material.

A further feature of the present invention is to provide dialysis systems which can regenerate or purify spent dialysis fluids with such sorbent cartridge systems.

Additional features and advantages of the present invention will be set forth in part in the description which follows, and in part will be apparent from the description, or may be learned by practice of the present invention. The objectives and other advantages of the present invention will be realized and obtained by means of the elements and combinations particularly pointed out in the written description and appended claims.

To achieve these and other advantages and in accordance with the purposes of the present invention, the present invention relates to a sorbent cartridge system, comprising a sorbent cartridge comprising i) a continuous sidewall extending between a fluid inlet and a fluid outlet, which define a chamber, ii) at least one layer comprising solid particulate media, wherein the at least one layer extends across the chamber within the continuous sidewall, and the at least one layer comprises a first region and a second region adjacent the first region and located closer to the continuous sidewall than the first region; and an intake manifold comprising at least one first fluid discharge port and at least one second fluid discharge port, wherein the intake manifold and sorbent cartridge are positionable with respect to each other to locate the first region of the sorbent cartridge for fluid communication with the at least one first fluid discharge port and locate the second region of the sorbent cartridge for fluid communication with the at least one second fluid discharge port, wherein the intake manifold is configured wherein a first volumetric flow rate of fluid discharged at the first fluid discharge port into the first region is greater as compared to a second volumetric flow rate of fluid discharged at the second fluid discharge port into the second region.

The present invention further relates to a method to regenerate or purify dialysis fluid comprising passing dialysis fluid through the sorbent cartridge system described herein.

The present invention further relates to a dialysis system to regenerate or purify spent dialysis fluid that includes one of the sorbent cartridge systems described herein.

It is to be understood that both the foregoing general description and the following detailed description are exemplary and explanatory only and are intended to provide a further explanation of the present invention, as claimed.

The accompanying drawings, which are incorporated in and constitute a part of this application, illustrate several embodiments of the present invention and together with the description, serve to explain the principles of the present invention.

BRIEF DESCRIPTION OF THE DRAWINGS

The drawings represent various design features of the sorbent cartridges of the present invention and comparison designs. Similar referencing identifiers in different figures can refer to similar features unless indicated otherwise. The drawings are not necessarily to scale.

DETAILED DESCRIPTION OF THE PRESENT INVENTION

Figure 1:
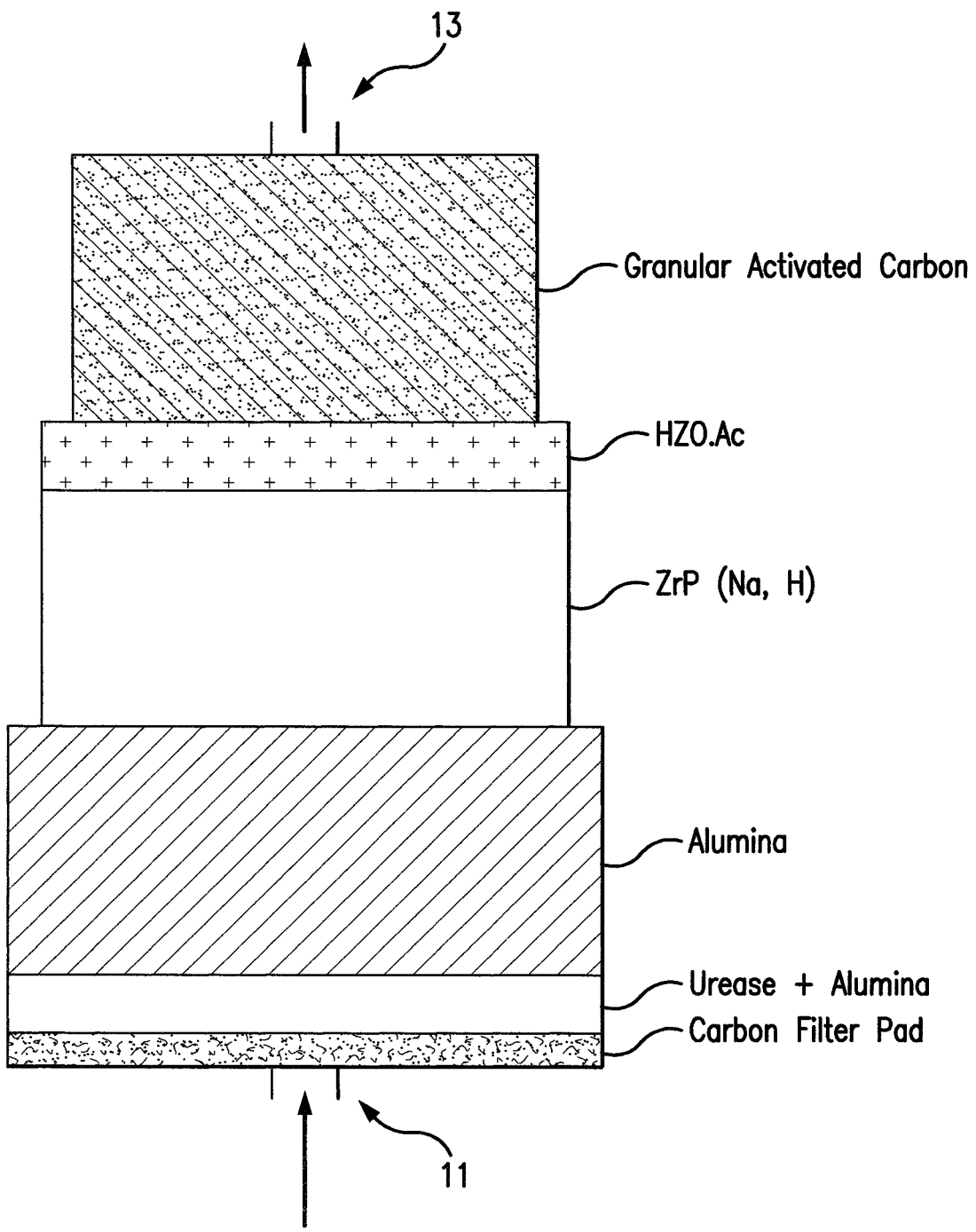
FIG. 1 is a schematic diagram showing a REDY® cartridge.
Figure 2:
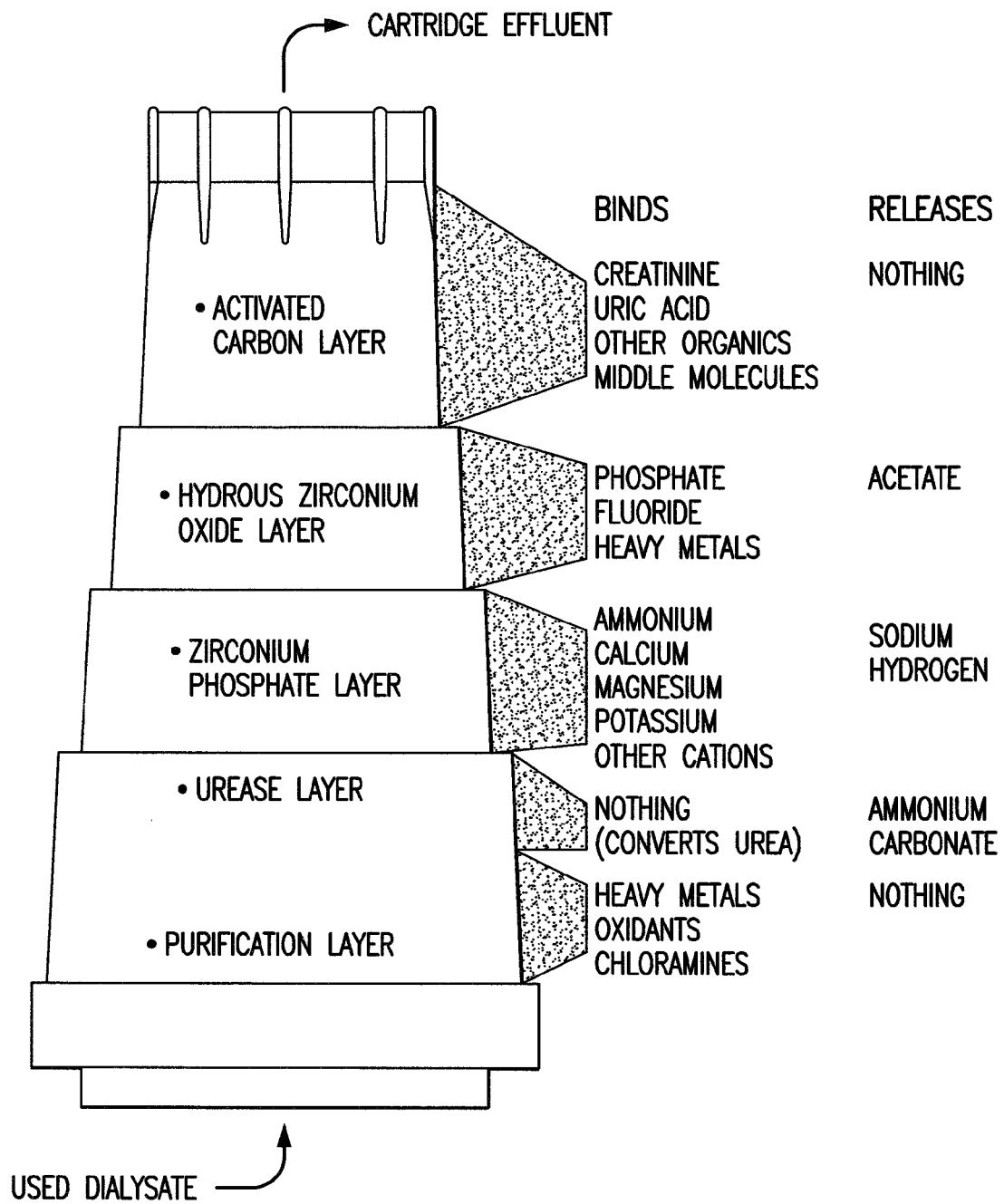
FIG. 2 is a diagram showing a cartridge and the various functions of each layer in a REDY® cartridge.

The present invention relates to cartridge system configurations for separation processes, such as the removal of waste products and excess fluid that accumulates in dialysate fluids, which can incorporate a dialysate fluid flow rate differential to provide improved flow distribution therein. As used herein, "flow rate" refers to volumetric flow rate (volume units/time units). As an option, one or more of packed bed particle layers in a sorbent cartridge packed with particles can be fed dialysate fluid differentially wherein an outer or peripheral region of the one or more layers receives fluid at a lower flow rate than an inner or central region of the same layer or layers. Flow distribution through the one or more layers can be maintained uniform or substantially uniform. The dialysate fluid can be inputted to the sorbent cartridge via a manifold or other flow control device which differentially controls dialysate fluid flow rate into one or more packed bed particle layers of the sorbent cartridge. As an option, the manifold's geometry is configured such that flow rate of dialysate fluid inputted near the periphery of the one or more packed bed particle layers is relatively lower compared to the flow rate of dialysate fluid inputted through the central region thereof. This can discourage fluid channel formation in the peripheral region of the sorbent cartridge particle layer or layers. This can provide improved efficient performance and/or avoid early or premature exhaustion of the cartridge.

As an option, the hydraulic diameter of the low flow rate branch(es), duct(s), pipe(s), conduit(s) or other fluid supplying structure which input dialysate fluid nearer to the periphery of the sorbent cartridge particle layer or layers is less than the hydraulic diameter of the higher flow rate branch (es), duct(s), pipe(s), conduit(s) or other fluid supplying structure that input dialysate fluid nearer to the central region of the sorbent cartridge particle layer or layers. These improved configurations can comprise packed bed particle and any other layered materials present in a container (i.e., a cartridge) capable of holding the layered materials useful for the separation process, wherein at least one or more or all of the particle bed containing layers present receive dialysate fluid at a differential flow rate as described herein.

As an option, the packed bed particle and other layered materials and the flow control manifold or other flow control device described in detail below can be used in a dialysis system or other similar type of system that is useful for the removal of waste products and/or excess fluid that accumulates in dialysate fluids, for instance, as a result of conducting dialysis. The sorbent cartridge can contain media in the form of a layer or layers having uniform or non-uniform density.

The manifold need not be integrated into the sorbent cartridge (though this can be done as an option, to provide a separately re-usable or disposable part from the sorbent cartridge. As an option, the manifold can be integrated into the dialysis machine itself with the sorbent cartridge modified to have corresponding input ports.

As described in more detail below, the present invention is useful in purifying or regenerating dialysate fluids used in peritoneal dialysis (PD) and in hemodialysis (HD). For purposes of the present invention, a dialysis solution means a peritoneal dialysis solution or dialysate fluids that are useful in hemodialysis or sorbent dialysis systems. Conventional dialysis solutions for PD or HD can be used and regenerated by the present invention and are known to those skilled in the art.

A sorbent cartridge which includes at least one layer(s) that is formed by a packed bed of solid particles of the same or substantially similar chemical composition (e.g., same chemical formula or analogs thereof or derivatives thereof), can have less than desired performance at times. Flow distribution in such a cartridge layer(s) can be non-uniform due to variations in hydraulic pressure and thus flow velocity and flow rates in different parts of the layer. The peripheral region of a packed bed of particles forming a cartridge layer that is located nearer to the cartridge wall than a central region of the same layer can be more liquid permeable. As a result, the liquid flowing through the cartridge therefore can tend to flow more through the peripheral region where there is less resistance to flow as compared to the central region wherein it is relatively more difficult for the fluid to penetrate. This can result in unused (or underused) material in the central region of the layer of the cartridge, whereas the peripheral region nearer to the cartridge wall can have overly-used material. This can lead to early or premature exhaustion of a cartridge component. For instance, flow distribution can be nonuniform in a layer of zirconium phosphate particles in a sorbent cartridge wherein a peripheral region of the layer is subjected to greater flow and thus greater usage than a central region of the same layer. If this occurs, ammonia breakthrough for the cartridge can occur earlier than if flow distribution had been uniform across the layer, thus shortening the useful life of the cartridge. Compounding this drawback, unused material, e.g., 10% to 15% by volume or other amounts, can be left in the layer or layers of the sorbent cartridge to be discarded. Sorbent cartridge designs would be preferred that can further reduce or prevent variations in flow distribution from occurring in packed bed particle layers of the sorbent cartridge. Accordingly, in the area of dialysis, it would be beneficial to overcome one or more of the above-described disadvantages associated with use of particles of similar kinds, sizes and morphologies arranged in a similar packing mode throughout a packed bed particle layer (or in multiple layers of the cartridge).

Figure 3:
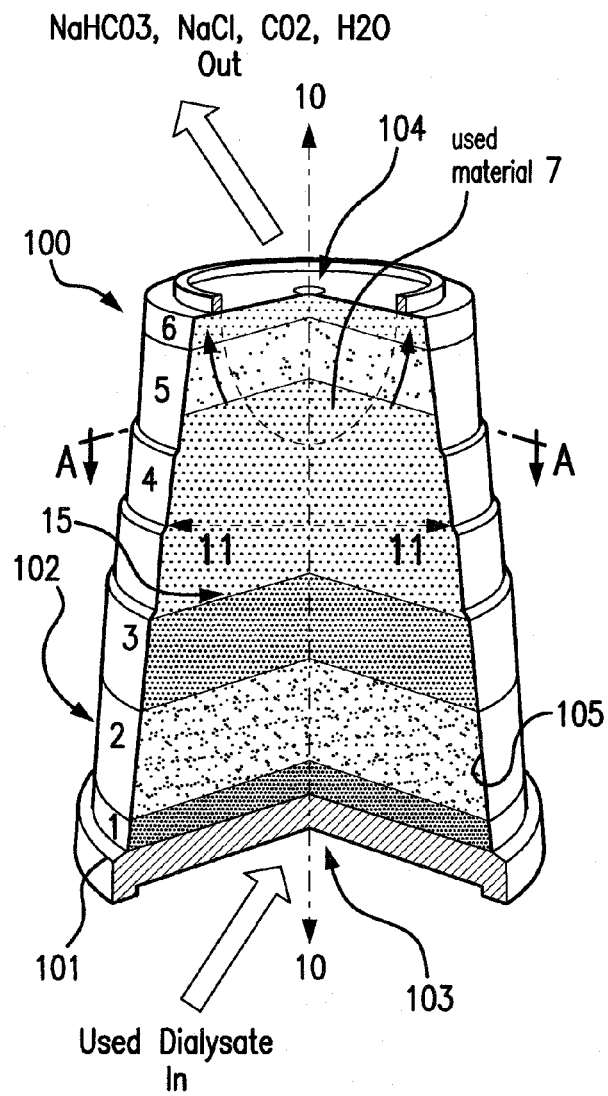
FIG. 3 is an exploded view of materials in a comparison example of a sorbent cartridge which has nonuniform flow distribution through layers thereof. Various intended functions of each layer of the cartridge are indicated.
Figure 3:
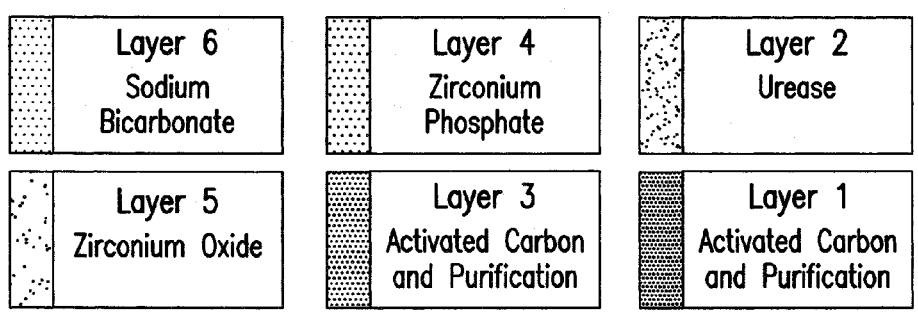

FIG. 3 shows a sorbent cartridge of a comparison example that is being used for treatment of dialysate fluid, which experiences differential hydraulic pressure and fluid flow through different regions of several layers of packed bed materials in the cartridge. The sorbent cartridge is identified in FIG. 3 as component 100, which has a housing 101, which comprises a solid continuous sidewall 102, inlet end wall 103, and outlet end wall 104, and a multi-layered sorbent bed 15 is incorporated within the housing 101. The sorbent bed 15 is shown here comprised of layers 1-6 and a central longitudinal axis 10-10, which extends through the sorbent bed 15 (usually coinciding with or near the geometric center of sorbent bed layers 1-6). The sorbent bed layers 1-6 extend in directions 11 radially outward (and usually orthogonally or substantially orthogonally (e.g., within 1 to 10 degrees of orthogonal)) from the central longitudinal axis 10-10 to an inner face (wall) 105 of the continuous sidewall 102 of the housing 101. In this configuration, each of layers 1-6 of the sorbent cartridge are comprised of material of similar chemical composition and physical properties per layer (e.g., particle size distribution, morphology, crystallinity and/or other properties). The particles used in these layers can be originally supplied in freely flowable solid particulate form. Once incorporated into the respective layers in the cartridge they are packed into layered beds comprising strata formed of the particles. Hydraulic pressure in the cartridge usually increases from layer to layer in the indicated direction of fluid flow through the sorbent cartridge, as expected from principles of hydraulics. In particular, there can be an uneven flow distribution within one or more of the individual cartridge layers that comprise a packed bed of particles. In the sorbent bed shown in FIG. 3, all or any lesser combination of layers 1-6 can be comprised of a packed bed of particles. These layers are shown here for sake of illustration, and other layers may be present in the alternative or in addition, or omitted from the cartridge. For purposes of this comparison example, at least the layer 4 is present and comprised of a packed bed of particles.

With regard to the cartridge of the comparison example shown in FIG. 3, a problem can occur wherein one or more of the individual layers of particles of the same or similar composition have a same or similar packed bed composition, particle distribution, crystallinity, and packing mode throughout the layer (e.g., within 10% for one or more of these properties), such as in a radial direction from a geometric center of the layer all the way to a peripheral edge thereof. If so, hydraulic pressure can be less in a peripheral region of the packed bed of particles forming at least one of the layers in the sorbent cartridge (e.g., a region nearer to the cartridge wall) as compared to a hydraulic pressure at the central region of the same layer that is located closer to the central axis of the cartridge. The fluid flow encounters less resistance to flow in the peripheral regions of layer or layers 4-6 as compared to the central region of the cartridge. This is undesirable as fluid flow can be channeled into the peripheral regions of layer 4-6 and diverted at least partially, essentially completely, or completely away from the central regions of these layers. This phenomenon is indicated by the arrows representing fluid flow directions that are shown in FIG. 3. This can result in unused (or underused) material 7 in the central region of at least one layer of the cartridge, whereas the peripheral region nearer to the cartridge wall can have overly-used material which becomes exhausted prematurely. This can impair the treatment performance and/or efficiency (e.g., urea capture efficiency) of the sorbent cartridge. The useful life of the cartridge can be shortened.

In FIG. 3, the region of unused material 7, which is identified by cross-hatching, has a parabolic profile that extends completely through layers 5 and 6 and partially through layer 4. This profile of the unused material is exemplary and not limited thereto. The unused material can be an amount, such as from about 10% to about 15% by volume or other amounts based on the volumes of any one or more of the indicated packed bed particle layers, and/or can have any geometric profile in the cartridge.

Figure 4:
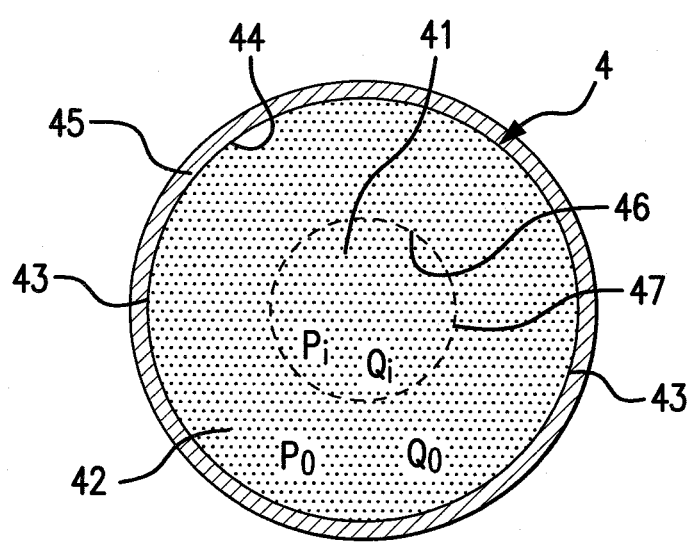
FIG. 4 is a cross-sectional view in direction A-A of the sorbent cartridge shown in FIG. 3.

FIG. 4 shows a hydraulic pressure $P_i$ and flow rate $Q_i$ in a central (inner) region 41 of layer 4 and pressure $P_o$ and flow rate $Q_o$ in the peripheral or outer region 42 of layer 4 in the sorbent configuration of FIG. 3 that has the indicated channeling problem. In this comparison example, the particles used to form layer 4 have the same particle size distribution and morphology throughout the cross-sectional area of the layer. The starting packing density of the constituent particles of layer 4 is the same throughout layer 4 including in the peripheral region 42 and the central region 41. The outer edge 43 of peripheral region 42 is contiguous with an inner face 44 of a sidewall 45 of the cartridge housing. During fluid flow through the sorbent cartridge 4, $P_o$ is or becomes less than ($<$) $P_i$ and $Q_o$ is or becomes greater than ($>$) $Q_i$ sufficient that fluid flows preferentially through the peripheral region of the layer as compared to fluid flow, if any, through the central region thereof. $P_o$ and $Q_o$ can represent a pressure or flow rate respectively that is present through all or essentially all (e.g., at least 75%, or 80%, or 90% by volume) of the packed bed of particles in outer region 42 which accommodates fluid flow completely through the layer. $P_i$ and $Q_1$ can represent a pressure or flow rate respectively that is present through all or essentially all (e.g., at least 75%, or 80% or 90% by volume) of the packed bed of particles in central region 41 which does not accommodate fluid flow through the central region 41. The outer region 42 has an inner edge 46 that is adjacent and contiguous with an outer edge 47 of the central region 41 that it encircles. In the arrangement of FIG. 4, the inner edge 46 of the outer region 42 completely surrounds the central region 41. FIG. 4 shows the peripheral and central regions (42, 41) arranged as concentric circles. Other cartridge shapes can encounter similar differential flow problems in the sorbent bed as the cartridge having the geometry shown in FIGS. 3 and 4.

Figure 5:
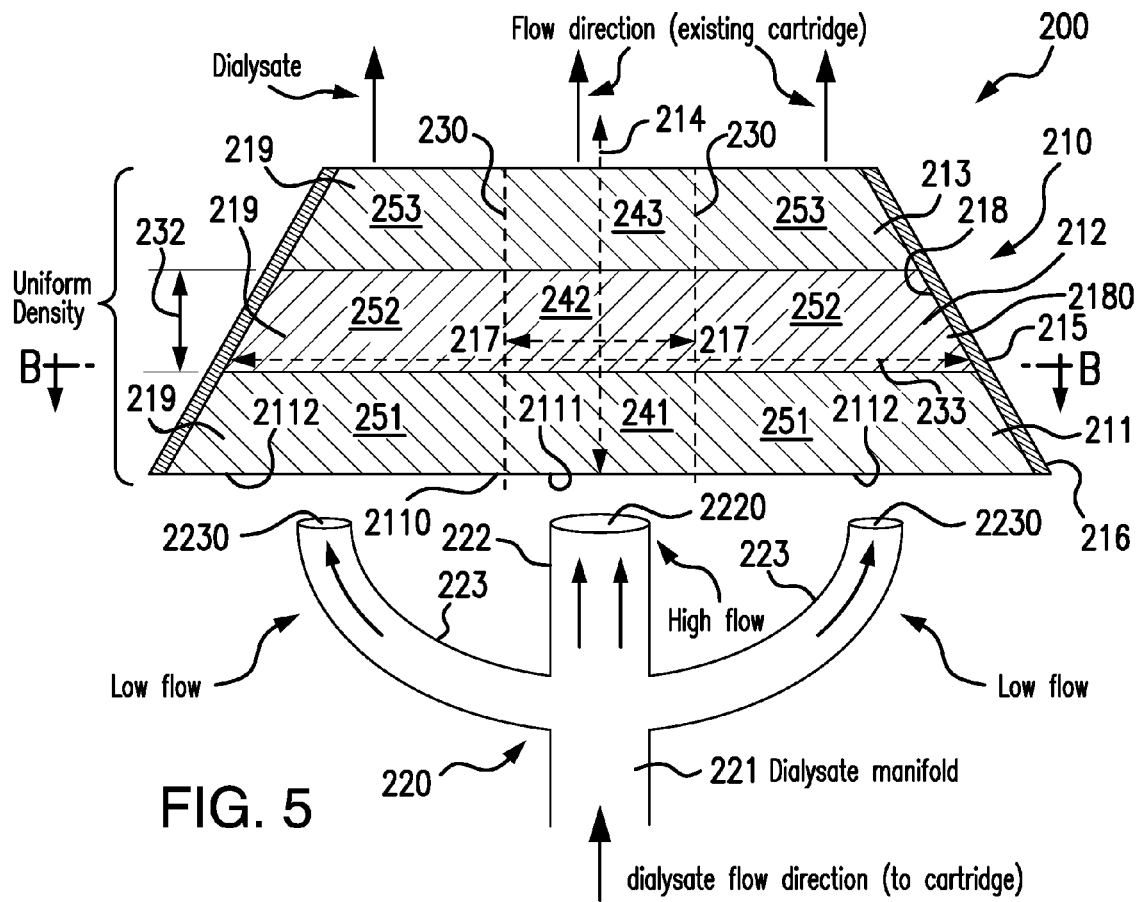
FIG. 5 is an exploded view of materials in one example of a sorbent cartridge system which has a sorbent cartridge and a manifold providing a flow rate differential in at least one particle layer of the sorbent cartridge according to an example of the present application.

Referring to FIG. 5, a sorbent cartridge system 200 is shown that includes a sorbent cartridge 210 and a dialysate manifold 220 according to an example. To facilitate the illustration, the discharge port or outlet 2220 of central branch 222 and the discharge ports or outlets of peripheral branches 223 of the manifold 220 are shown as slightly spaced apart from the inlet opening or face 2110 of the sorbent cartridge, as indicated by the dashed lines. In use, the outlets 2220 and 2230 of branches 222 and 223 of the manifold 220 can be attached to matching ports or located adjacent to a fluid permeable membrane associated with inlet opening (face) 2110 of the sorbent cartridge 210, which arrangements are shown in more detail in other figures described herein, wherein dialysate or other fluid can flow directly into the sorbent cartridge 210 from the manifold 220 in a sealed fluid-tight manner without leakage or other loss of fluid from the system.

The sorbent cartridge 210 is shown as including a layer 211 (e.g., urease layer 211), layer 212 (e.g., zirconium phosphate layer 212), and layer 213 (e.g., hydrous zirconium oxide layer 213). These layers are shown here for sake of illustration, and the concepts described herein are not at all limited to these layers or types of layers. The sorbent cartridge preferably includes at least one particle layer to take advantage of the improvements and benefits of the present invention. Sorbent cartridge 210 may include additional treatment and other functional layers not shown in this illustration. The sorbent cartridge 210 has a central axis 214 that extends through the layers 211, 212 and 213 and any other layers in the cartridge (usually coinciding with or near the geometric center of sorbent bed layers 211-213). The central axis 214 extends longitudinally through the geometric center of the shape of the cartridge housing 215 defined by its continuous sidewall 216. The sidewall 216 forms a continuous enclosure around the outer edges of the layers incorporated within the cartridge. The first, second, and third sorbent layers 211, 212, and 213 can be centered about central axis 214. The sorbent bed layers 211-213 extend in directions 217 radially outward (and usually orthogonally or substantially orthogonally) from the central axis 214 to an inner face 218 of a continuous sidewall 216 of the cartridge housing 215. The cartridge 210 can have an inlet end wall and outlet end wall (not shown) similar to housing 100 shown in FIG. 3, or can have other designs, which can be modified to support simultaneous introduction of fluids from multiple ports of the manifold 220. Each of layers 211-213 can be formed of particles shaped into a disc-shaped component having an overall thickness that is uniform or substantially uniform throughout the respective layer, and a diameter in the radial direction which, in this example, gradually decreases through the thickness of the respective layer in the direction of fluid flow with respect to the central axis 214. Layer 212, for example, is shown in FIG. 5 with thickness 232 (vertical) and a diameter 233 (radial). Layers 211 and 213 can have thicknesses and diameters that are oriented in similar respective directions. Layers 211-213 together can be referred to as a sorbent bed 219 for purposes of this illustrated cartridge.

In the cartridge configuration shown in FIG. 5, layers 211-213 of the sorbent cartridge are each comprised of material of the same or similar chemical composition for that layer. Each of the layers 211-213 can have uniform packing densities throughout each layer. In one option, the packing densities are the same in all regions of each layer of the sorbent bed 219, inclusive of a central region 241, 242, 243 (e.g., far from wall), such as locations of a layer radially within lines 230 in layers 211, 212, 213, respectively, or a peripheral region 251, 252, 253 (e.g., near wall), such as locations of a layer radially outside lines 230 and within the inner face 218 of the wall for layers 211, 212, 213, respectively. The location of lines 230 in this illustration can be arbitrary for purposes of the illustration to the extent a central region is identified that is surrounded by the peripheral region so that the central region does not directly adjoin an inner wall face of the sorbent cartridge. The location of lines 230 can define a central region in the sorbent bed that would contain underused material if the sorbent cartridge is not used in combination with an intake manifold as described herein.

The peripheral region can be from 1% to 50% of the cross-sectional area of the layer, such as 1%, 5%, 10%, 15%, 20%, 25%, 30%, 35%, 40%, 45% or 50%. The central region can be from 10% to 80% of the cross-sectional area of the same layer, such as 10%, 15%, 20%, 25%, 30%, 35%, 40%, 45%, 50%, 55%, 60%, 65%, 70%, 75%, or 80%. A uniformity in packing density including the central and peripheral regions can be provided in at least one or more or all of the particle layers 211-213 as installed in the sorbent cartridge 210 before use (i.e., before flowing dialysate or other fluid through the cartridge).

The average packing density in the central region compared to the peripheral region of any particle layer of the sorbent bed can vary by less than ±5%, or vary by less than ±2%, or vary by less than ±1%, or vary by less than ±0.5%, or vary by less than ±0.1%, or other values (e.g., when the particle layer(s) is wet, such as uniformly wet). As an option, in the sorbent bed 219 shown in FIG. 5, the particles in inner region 242 of layer 212 have a packing density ($D_{p1}$) that varies by less than ±1% from the packing density ($Dp_2$) of the particles in outer region 252 of layer 212. The layer 212 can have such uniformity in packing density in a radial direction extending from a geometric center of the layer (e.g., coinciding with central axis 214) towards a peripheral edge 2180 of layer 212. Any of layers 211, 213, and/or other particle layers in the sorbent bed 219 can have similar uniformity in particle density.

Still referring to FIG. 5, in layer 212 (and similarly with respect to layer 211 and 213), the respective particles in central region 242 and peripheral region 252 of layer 212 can be incorporated into the cartridge having similar physical properties, e.g., particle size distribution, packing mode, crystallinity and/or other properties. Though the sorbent cartridge in FIG. 5 is shown with a tapered shaped sidewall, which has a diameter that smoothly tapers inward towards the outlet end, the indicated concepts described herein can be applied to cartridges that have other shapes, such as cylindrical, rectangular (e.g., square), hexagonal, or other shapes. The shape can be straight-edged, tapered, stepped, or other shapes. Any geometric shape can generally be used.

Figure 6:
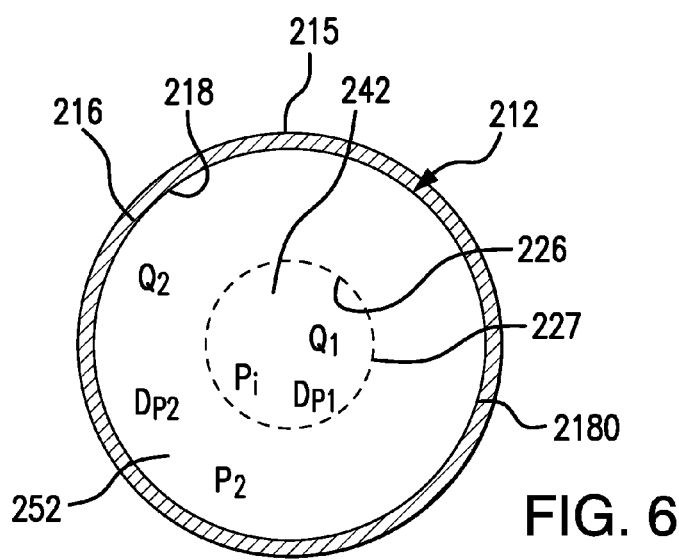
FIG. 6 is a cross-sectional view in direction B-B of the sorbent cartridge shown in FIG. 5 according to an example of the present application.

FIG. 6 shows a packing density $D_{p1}$, hydraulic pressure $P_1$, and flow rate $Q_1$ in the central (inner) region 242 of layer 212 and a packing density $D_{p2}$, hydraulic pressure $P_2$ and flow rate $Q_2$ in the peripheral (outer) region 252 of layer 212 in the sorbent bed 219 of the cartridge 210 shown in FIG. 5. The outer edge 2180 of peripheral region 252 is contiguous with the inner face 218 of a sidewall 216 of the cartridge housing 215. As indicated, $D_{p1}$ is the same or essentially the same as $D_{p2}$, and the flow rate $Q_2$ of fluid passing through peripheral region 252 is the same or essentially the same as the flow rate $Q_1$ of fluid passing through central region 242 of the cartridge from use of the manifold such as described herein, in combination therewith. For this illustration, the peripheral region 252 has an arbitrary inner edge 226 that is adjacent and contiguous with an arbitrary outer edge 227 of the central region 242 that encircles it. FIG. 6 shows the peripheral and central regions (252, 242) arranged as concentric circles. Other shapes of the cartridge can dictate different shapes of these regions. For example, a cartridge with a square (or rectangular) cross-sectional shape which has sorbent bed layers loaded therein with complementary geometry can have peripheral and central regions of differential flow created therein that comprise a square-shaped central region inset within an outer square-shaped ribbon of material at the periphery of the layer (not shown).

Hydraulic pressure in a sorbent cartridge, such as shown in FIG. 5, usually increases from layer to layer in the indicated direction of fluid flow through the sorbent cartridge, as expected from hydraulic principles. Packing density usually is positively correlated with the magnitude of hydraulic pressure that occurs in the respective region of the layer in use. Higher packing density correlates with higher hydraulic pressure and relatively lower packing density correlates with lower hydraulic pressure. Absent external effects, a particle layer formed of uniform packing density should correlate with uniform hydraulic pressure in the layer. However, it has been found that a wall effect of the housing 218 on the packed bed layers 211-213 or other packed bed layers included can result in reduced flow resistance in the outer or peripheral region 251, 252, and/or 253 of layers 211, 212 and/or 213 as compared to the inner or central region 241, 242, and/or 243 of layers 211, 212, and/or 213, respectively. If not countered or compensated for, the wall effect can lead to the indicated channeling of flow through an outer region 251, 252, and/or 253 at the expense of flow through an inner region 241, 242, and/or 243 of layer 211, 212, and/or 213, respectively. As indicated, this can lead to inefficient operation and significant unused or underused material in the sorbent cartridge when other portions become prematurely exhausted.

To prevent, offset, or substantially offset wall effect on fluid flow in the outer region 251, 252, and/or 253 of layer 211, 212, and/or 213 to reduce or eliminate channeling phenomenon in the layer, a manifold or other flow control device is used to supply dialysate fluid to the sorbent cartridge, which provides a flow rate differential in fluid supplied nearer to the peripheral region as compared to central region of the particle layer(s) in the sorbent bed of the sorbent cartridge. The manifold 220 can differentially control fluid flow into the sorbent bed 219 of the sorbent cartridge 210 to provide a greater flow rate at the central region as compared to the flow rate concurrently provided at the peripheral region of at least one or more or all of the particle layers as installed in the sorbent cartridge during flow of dialysate or other fluid through the sorbent cartridge in use thereof. By providing differential flow rates fed into separate regions of the same particle layer with respect to each other, fluid flow can be enabled to occur simultaneously through inner region 241, 242, and/or 243 and outer region 251, 252, and/or 253 of layers 211, 212, and/or 213 and/or other particle layers, wherein channel formation in a peripheral region of a packed bed of particles forming one or more or all of the particle layers in the sorbent cartridge (e.g., a region nearer to the cartridge wall) can be discouraged or prevented.

As an option, the intake manifold is configured wherein the total volumetric flow rate of fluid discharged at a fluid discharge port into the central region of at least one particle layer of the sorbent bed of the sorbent cartridge is at least 5% greater, or at least 10% greater, or at least 15% greater, or at least 20% greater, or at least 25% greater, or at least 30% greater, or greater, or from 5% to 30% greater, or from 5% to 25% greater, or from 5% to 20% greater, or from 5% to 15% greater, as compared to the total volumetric flow rate of fluid discharged at a fluid discharge port(s) into the peripheral region of the at least one particle layer.

Referring to FIG. 5, the intake manifold 220 can be configured wherein the total volumetric flow rate of fluid discharged at the fluid discharge port 2230 into the central region 241 of at least one particle layer 211 (and/or central region of 212 and/or 213) of the sorbent bed 219 of the sorbent cartridge 210 is at least 5% greater, or at least 10% greater, or at least 15% greater, or at least 20% greater, or at least 25% greater, or at least 30% greater, or greater, or from 5% to 30% greater, or from 5% to 25% greater, or from 5% to 20% greater, or from 5% to 15% greater, as compared to the total volumetric flow rate of fluid discharged at the fluid discharge port 2230 into the peripheral region 251 of the same particle layer(s). The volumetric flow rates can be expressed in units of mL/minute, or other appropriate units. The volumetric flow rates can be measured at the fluid emergent discharge openings or ports of the manifold or in-line within the branches, and for the sorbent cartridge, at the bottom (inlet) surface or top (outlet) surface of a particle bed layer. The measurement of the volumetric flow rates can be done in a manner known in the industry, such as using local sensors and flow meters.

The flow rate differential provided with the manifold or other device set up can be maintained for at least the predominance, essentially all, or all of a dialysis treatment session. As an option, in a process using the sorbent cartridge system such as described herein in a dialysis treatment performed on a patient, the dialysis fluid can be passed through the sorbent cartridge system for a treatment session having a duration of 180 minutes to 300 minutes, wherein the dialysis fluid flows concurrently through the central region at a first fluid flow rate and through the peripheral region at a second fluid flow rate, wherein the first fluid flow rate is at least 5% more, or at least 10% more, or at least 15% more, or at least 20% more, or at least 30% more, or from 5% to 30% more, or from 5% to 20% more, or from 5% to 15% more, or other amounts, than the second fluid flow rate for at least 90%, or at least 92%, or at least 94%, or at least 96%, or at least 98%, or at least 99%, or for 100%, of the treatment session.

The indicated provision of a differential flow rate between the peripheral (outer) and central (inner) regions of a particle layer or layers of a sorbent bed can reduce the occurrence of unused (or underused) material in the central region of layer 211, 212, and/or 213 and/or other particle layers of the cartridge, and reduce the risk of the cartridge materials being exhausted prematurely, as compared to a similar cartridge design that receives dialysate at the same flow rate in both central and peripheral regions thereof. This can improve treatment performance and/or efficiency (e.g., urea capture efficiency) of the sorbent cartridge. The unused material in a particle bed containing layer of a sorbent cartridge used with a manifold described herein can be reduced to 5% or less by volume, such as from 0 to about 5% by volume, or from about 1% to about 5% by volume, or from about 1% to about 4% by volume, or from about 1% to about 3% by volume, or other amounts, based on volume of the indicated packed bed particle layer (and a single full dialysis treatment session).

Figure 7:
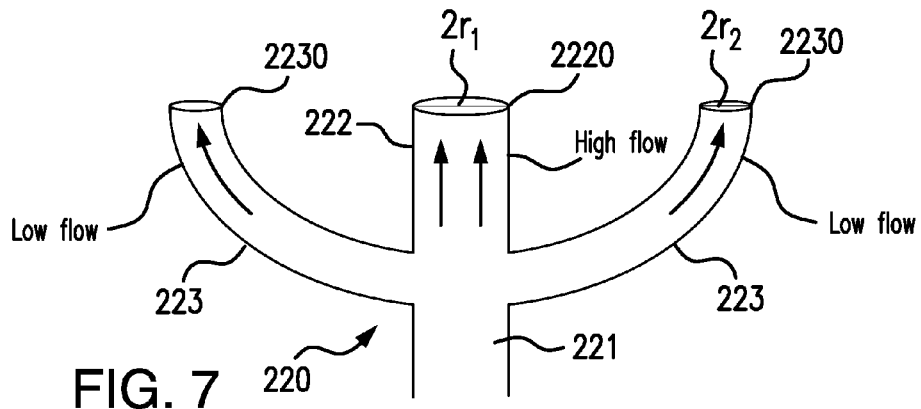
FIG. 7 is a perspective view of the manifold shown in FIG. 5 according to an example of the present application.

Referring to FIG. 7, an intake manifold 220 according to an example of the present application is shown, such as the one used in the system shown in FIG. 5, which comprises a fluid feed passageway 221 which receives spent dialysate fluid from a dialyzer or other fluid (not shown), which is branched into at least one central branch passageway 222 comprising at least one discharge port 2220 which have a hydraulic diameter (i.e., $2r_1$), which supplies a portion of the dialysate fluid to the central region of a particle layer or layers of the sorbent bed of the sorbent cartridge, at least one peripheral branch passageway 223 comprising at least one discharge port 2230 which have a hydraulic diameter (i.e., $2r_2$), which supplies the remainder of the dialysate fluid to the peripheral region of the particle layer or layers of the sorbent bed of the sorbent cartridge. The fluid feeding passageway 221 supplies dialysate fluid concurrently to the at least one central branch passageway 222 and the at least one peripheral branch passageway 223. The hydraulic diameter ($2r_1$) of the fluid discharge port 2220 of the at least one central branch passageway 222 is greater (larger) than the hydraulic diameter ($2r_2$) of the fluid discharge port 2230 of the at least one peripheral branch passageway 223 to provide the indicated flow rate differential between the indicated inner and outer branches. The central branch passageway 222 and the peripheral branch passageway(s) 223 can be supplied from a common fluid source at the same supply fluid pressure and flow rate in the main feed branch 221 of the manifold, wherein the differences in sizes of the central and peripheral passageways thereof create different flow rates depending on the relative discharge port or opening sizes. The central discharge port or opening 2220 and the ports or openings 2230 of the peripheral branches are illustrated as circular in this and other embodiments herein. Other opening geometries for the discharge ports of the manifold may be used, such as oval, square, rectangle, triangular, criss-cross, star, or other shapes.

Figure 8:
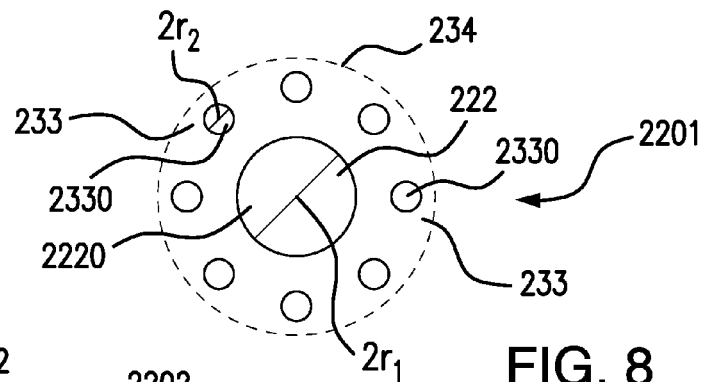
FIG. 8 is a cross-sectional view of another configuration of the manifold according to an example of the present application.

FIG. 8 shows another configuration of a manifold 2201 according to an example of the present application wherein the at least one peripheral branch passageway comprises a plurality of pipes 233 having respective fluid discharge openings 2330 arranged in spaced-apart pattern around the at least one fluid discharge port 2220 of the at least one central branch passageway 222, wherein each of the plurality of pipes 233 have a hydraulic diameter $2r_2$ at the openings 2330. The number of pipes 233 can be 2, 3, 4, 5, 6, 7, 8, 9, 10, 11, 12 or more or another number. The pipes 233 can be equidistantly spaced, such as in a circular pattern, or spaced in another pattern, around the at least one central discharge port 2220. The hydraulic diameter $2r_1$ of the opening 2220 of the at least one central branch passageway 222 is greater than the hydraulic diameter $2r_2$ of each opening 2330 of the pipes 233 to provide the indicated flow rate differential between the indicated inner and outer branches. The plurality of pipes 233 and central branch passageway 222 may be housed within a larger diameter pipe, conduit, hose, or similar passageway 234.

Figure 9:
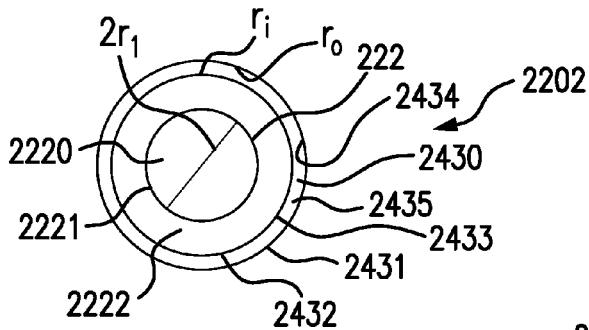
FIG. 9 is a cross-sectional view of another configuration of manifold according to an example of the present application.

FIG. 9 shows another configuration of a manifold 2202 according to an example of the present application, wherein the at least one peripheral branch passageway comprises a single duct 2435 having a continuous discharge opening 2430 which is arranged around and radially spaced from the at least one discharge port 2220 of the at least one central branch passageway 222, wherein the single duct 2435 having a hydraulic diameter of $2(r_o-r_i)$ for its opening 2430, wherein $r_o$ is the outer diameter of the opening 2430 of duct 2435 and $r_i$ is the inner diameter of the opening 2430 of duct 2435. A space 2222 is defined between the outer wall 2221 that defines the inner passageway 222 and the wall 2432 which defines the inner wall of the duct 2435. The inner diameter $r_i$ of the opening 2430 of the duct 2435 is defined by the outer wall face 2433 of wall 2432, and the outer diameter $r_o$ of the opening 2430 of duct 2435 is define d by the inner wall face 2434 of the outer wall 2431. The hydraulic diameter $2r_1$ of the discharge opening 2220 of the at least one central branch passageway 222 is greater than the hydraulic diameter of $2(r_o-r_i)$ of the opening 2430 of the duct 2435 to provide the indicated flow rate differential between the indicated inner and outer openings.

Figure 10:
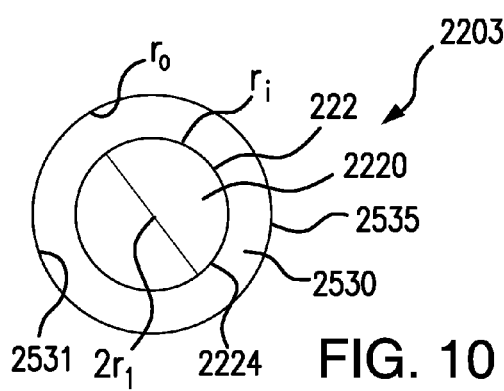
FIG. 10 is a cross-sectional view of another configuration of a manifold according to an example of the present application.

FIG. 10 shows another configuration of a manifold 2203 according to an example of the present application wherein the intake manifold 2203 comprises concentric tubes comprising an inner tube 222 comprising a discharge opening 2220 having a hydraulic diameter ($2r_1$), and an outer tube 2535 concentrically surrounding the inner tube 222, wherein the outer tube 2535 comprises a discharge opening 2530 having a hydraulic diameter of $2(r_o-r_i)$. The inner diameter $r_i$ of the opening 2530 of the tube 2535 is defined by the outer wall face 2224 of tube 222 and the outer diameter $r_o$ of the opening 2530 of outer tube 2535 is defined by the inner wall face 2531 of the outer tube 2535. The hydraulic diameter $2r_1$ of the discharge opening 2220 of the inner tube 222 is greater than the hydraulic diameter of $2(r_o-r_i)$ of the discharge opening 2530 of the outer tube 2535 to provide the indicated flow rate differential between the indicated inner and outer branches.

The peripheral pipes, tubes, or ducts and the central passageway of the manifold, and housing pipe if used, or any other parts of the manifold, as used in this embodiment or any others described herein, can be any liquid tight solid material that can be shaped or formed into the desired shapes of the parts, such as plastic, metal, metal alloys, glass, ceramic, composite hose, or other materials. The pipes and passageway may be rigid or flexible plastic, such as thermoplastic or rubber tubing (e.g., tubing made of polypropylene or other polyolefin, silicone, polyurethane, polyvinyl chloride or other fluoropolymer, cured natural and/or synthetic rubber, or others). If a housing pipe is used in the manifold, it may be preferable to select a more rigid material for that part.

Figure 11:
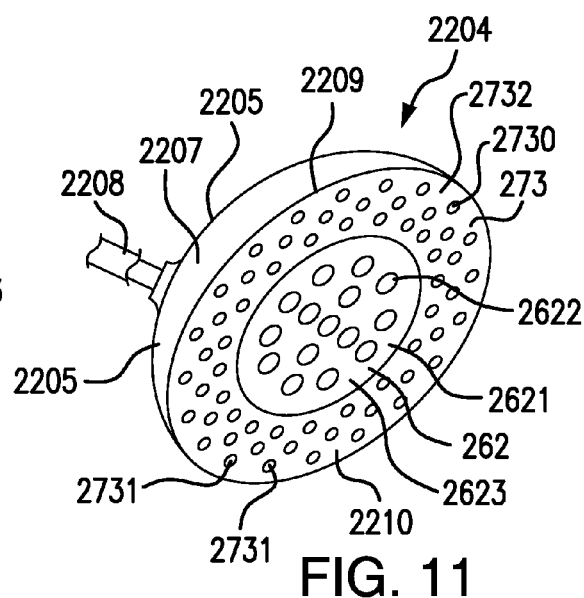
FIG. 11 is a perspective view of another configuration of the manifold according to an example of the present application.

FIG. 11 shows another configuration of a manifold 2204 according to an example of the present application wherein the manifold 2204 comprises a spray nozzle head 2205 comprising a housing 2206, which defines a fluid chamber 2207 which is fluidly linkable with a dialysate fluid supply line 2208 that can be connected with a dialyzer (not shown), and an opposite internal open side 2209 which fluidly communicates with a perforated plate 2210 covering the open side 2209 of the housing 2206. The perforated plate 2210 can comprise a central region 262 comprising a perforated plate portion 2621 defining a plurality of fluid discharge holes 2622 passing through a solid plate portion 2623, wherein the holes 2622 have a hydraulic diameter (e.g., $2r_1$ for round holes), and a peripheral region 273 which surrounds the central region 262. The peripheral region 273 can comprise a perforated plate portion 2730 defining a plurality of fluid discharge holes 2731 passing through a solid plate portion 2732, wherein the holes 2731 have a hydraulic diameter (e.g., $2r_2$ for round holes). The hydraulic diameter (e.g., $2r_1$) of the holes 2622 in the central (inner) region 262 are larger than the hydraulic diameter (e.g., $2r_2$) of the holes 2731 in the peripheral (outer) region 273 to provide an indicated flow rate differential in fluid discharged from holes 2622 in the indicated central region 262 and the holes 2731 in the peripheral region 273 of the perforated plate 2210. The spray nozzle head and components thereof can be constructed of any of the same materials indicated above for the manifold.

Figure 12:
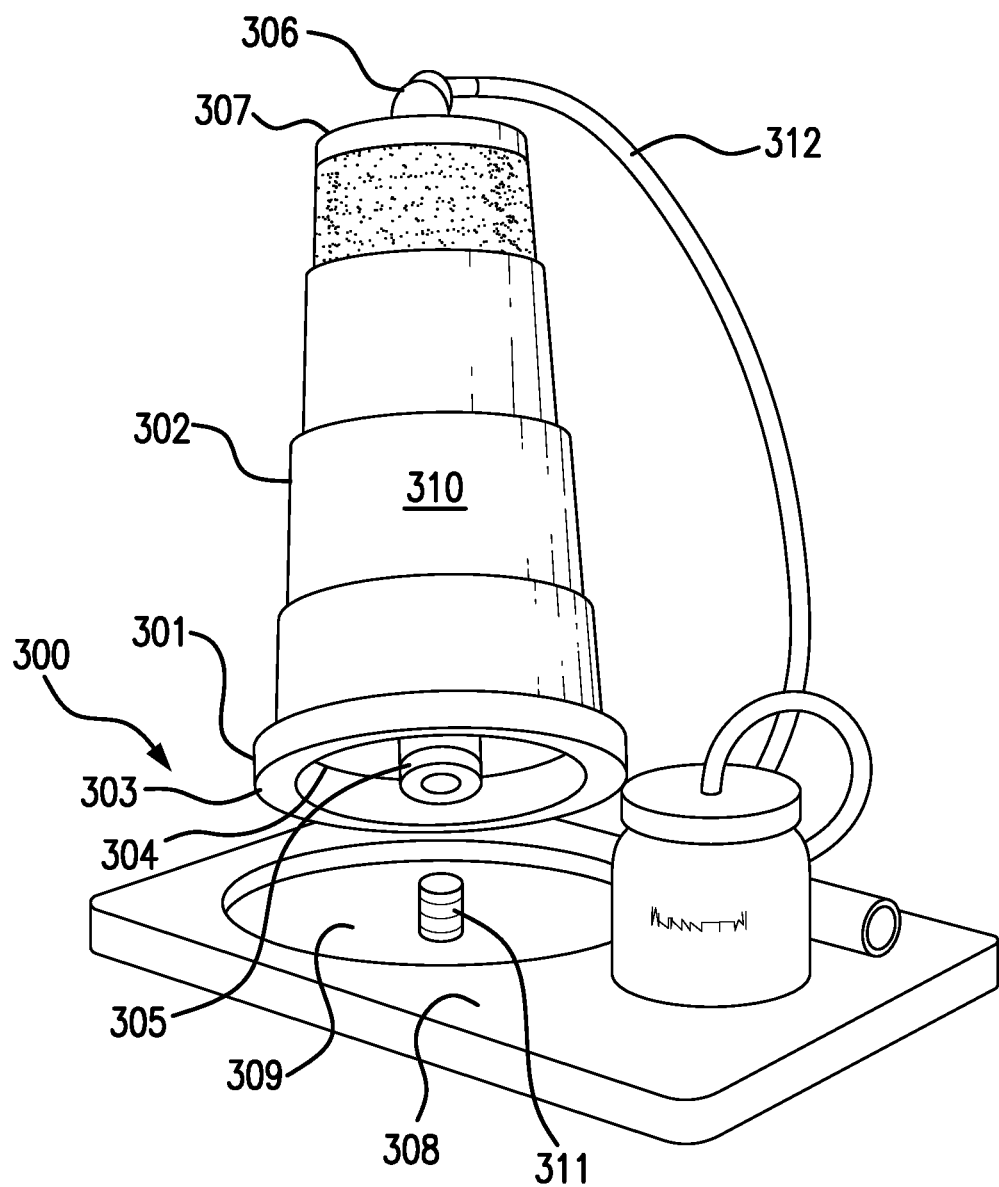
FIG. 12 is a perspective view of a sorbent cartridge mount according to a comparison example.

The sorbent cartridge and the intake manifold can be configured to be detachably mountable to each other. For comparison, FIG. 12 shows a dialysis system sorbent cartridge mount 300, which has been used for a sorbent cartridge 310 of the kind shown in FIG. 3. The bottom end 301 of the cartridge housing 302 has a downward extending circular skirt or collar 303 which defines a recess 304 at the bottom end 301 of the housing 302. At its bottom end 301, the cartridge 310 has a fluid input port 305 extending into the recess 304, and a fluid discharge port 306 at its opposite top end 307. To mount the cartridge 310 for use with a dialysis machine (not shown), cap plugs (not shown) are removed from the cartridge ports 305 and 306, and the cartridge 310 is placed in a storage slot 309 of a cartridge shelf 308. The cartridge 310 is seated securely on the cartridge shelf 308 with the cartridge port 305 firmly attached to a base nipple 311 in the storage slot 309 of the cartridge shelf 308, and tubing 312 is connected to the top port 306 of the cartridge 310. The base nipple 311 is supplied with fluid under pressure at an opposite hidden end in this view (not shown).

Figure 13:
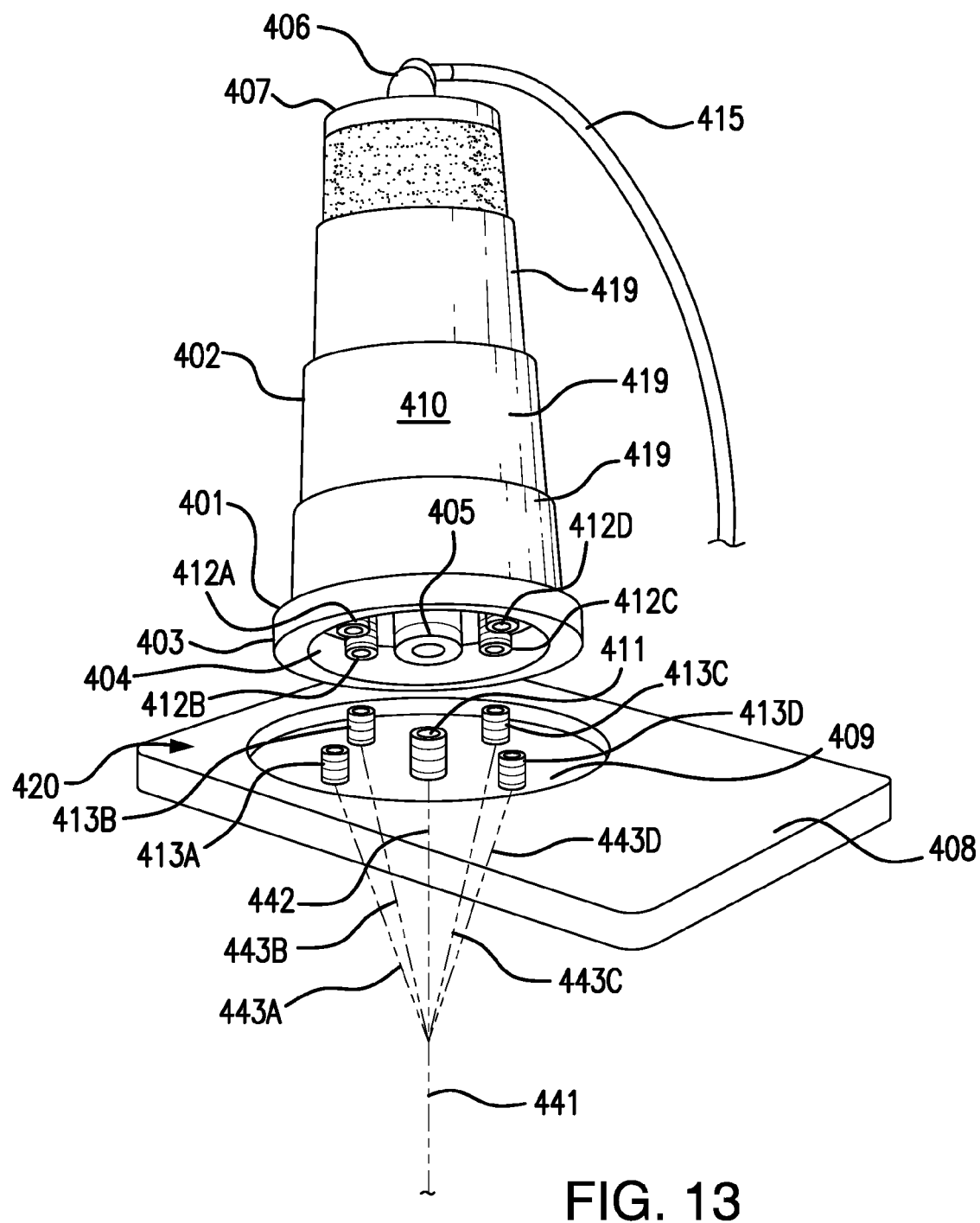
FIG. 13 is a perspective view of a manifold and sorbent cartridge mount configuration for making a releasable connection of these parts in a sorbent cartridge system according to an example of the present application.

As indicated, in the present invention, the intake manifold used in combination with the sorbent cartridge simultaneously inputs multiple streams of fluids into a particle layer of the sorbent cartridge at different flow rates, with the flow rates provided depending on whether the fluid stream is closer or further away from the inner wall of the cartridge housing. Referring to FIG. 13, as an option, an intake manifold 420 and sorbent cartridge 410 can have matching multi-ported ends for making a releasable connection of these parts according to an example of the present application. The sorbent cartridge 410 has a bottom end 401, a top end 407 and contains a sorbent bed 419 including at least one particle layer within a housing 402. At the top end 407, tubing 415 is connected to the top port 406 of the cartridge 410. The bottom end 401 of the cartridge housing 402 can have a downward extending circular skirt or collar 403 which defines a recess 404 at the bottom end 401 of the housing 402. At its bottom end 401, the cartridge 410 can have a central fluid input port 405 and plural peripheral fluid input ports 412A, 412B, 412C and 412D that surround the central port 405 and also extend into the recess 404, and a fluid discharge port 406 at its opposite top end 407. Central fluid input port 405 has a larger fluid input opening than that of the plural peripheral fluid input ports 412A, 412B, 412C and 412D. To mount the cartridge 410 for use with a dialysis machine (not shown), cap plugs (not shown) can be removed from the cartridge ports 405, 412A-D, and 406, and the cartridge 410 can be placed in a storage slot 409 of a cartridge shelf 408 of the manifold 420, wherein the cartridge 410 is seated securely on the cartridge shelf 408 of the manifold 420 with the cartridge port 405 firmly attached to a central base nipple 411 in the storage slot 409 and the cartridge ports 412A-D firmly attached to smaller base nipples 413A-D of the manifold 420. The base nipples 411 and 413A-D can be simultaneously supplied with fluid under pressure at opposite hidden ends below shelf 408 within the manifold 420. The base nipples 411 and 413A-D can be fluidly connected (e.g., by tubing or piping), to a common fluid supply line (indicated schematically by 441) via individual fluid line branches (indicated schematically by 442 and 443A-D). As indicated, the base nipples 411 and 413A-D can be supplied from a common fluid source at the same supply fluid pressure and flow rate wherein the differences in sizes of the central and peripheral nipples create different flow rates depending on the relative discharge opening sizes thereof. The cartridge ports 405 and 412A-D at the bottom end 401 of the cartridge 410 are arranged in a pattern that matches with the pattern of the base nipples 411 and 413A-D on the cartridge shelf 408 of manifold 420. The base nipple 411 on the cartridge shelf 408 of the manifold 420 defines a larger discharge opening for larger flow rate than the smaller discharge openings defined by base nipples 413A-D for lower flow rates, such as described in previous FIGS. 5-11. In view of this, the cartridge port 405 preferably can define a fluid input opening that corresponds with that of the larger base nipple 411, which is larger than the opening defined by each of cartridge ports 412A-D, which can have a smaller size corresponding to the size of the discharge openings of the smaller base nipples 413A-D of the manifold 420. One central cartridge port and four peripheral ports, and one central base nipple and four peripheral smaller base nipples, are shown in FIG. 13, and different matching numbers of these components can be used (e.g., 1 larger central nipple and 2, 3, 5, 6, 7, 8, 9, 10, 11, 12 or more or any other number of smaller base nipples on the manifold and a corresponding number and pattern of central and peripheral ports on the bottom end of the sorbent cartridge). This connection strategy for the sorbent cartridge and manifold can be adapted to be applied to any of the manifold configurations shown in FIGS. 5-11.

As another option, the sorbent cartridge and the intake manifold can be releasably attached without using multiple fluid entry ports on the bottom end of the sorbent cartridge. In this respect, the sorbent cartridge and the intake manifold may have threaded ends or radially interlockable tabs and flanges that can be mated together using manual twisting force. If the sorbent cartridge and manifold have matching threaded ends, the sorbent cartridge can be screwed into position on an upper end of the manifold to make a releasable fluid tight connection therewith, wherein the smaller diameter peripheral discharge port or ports of the manifold can be brought into adjoining alignment with a peripheral region of particle layers of the sorbent bed of the sorbent cartridge and concurrently the larger diameter central discharge port or ports of the manifold can be brought into adjoining alignment with a central region of particle layers of the sorbent bed of the sorbent cartridge.

Figure 14:
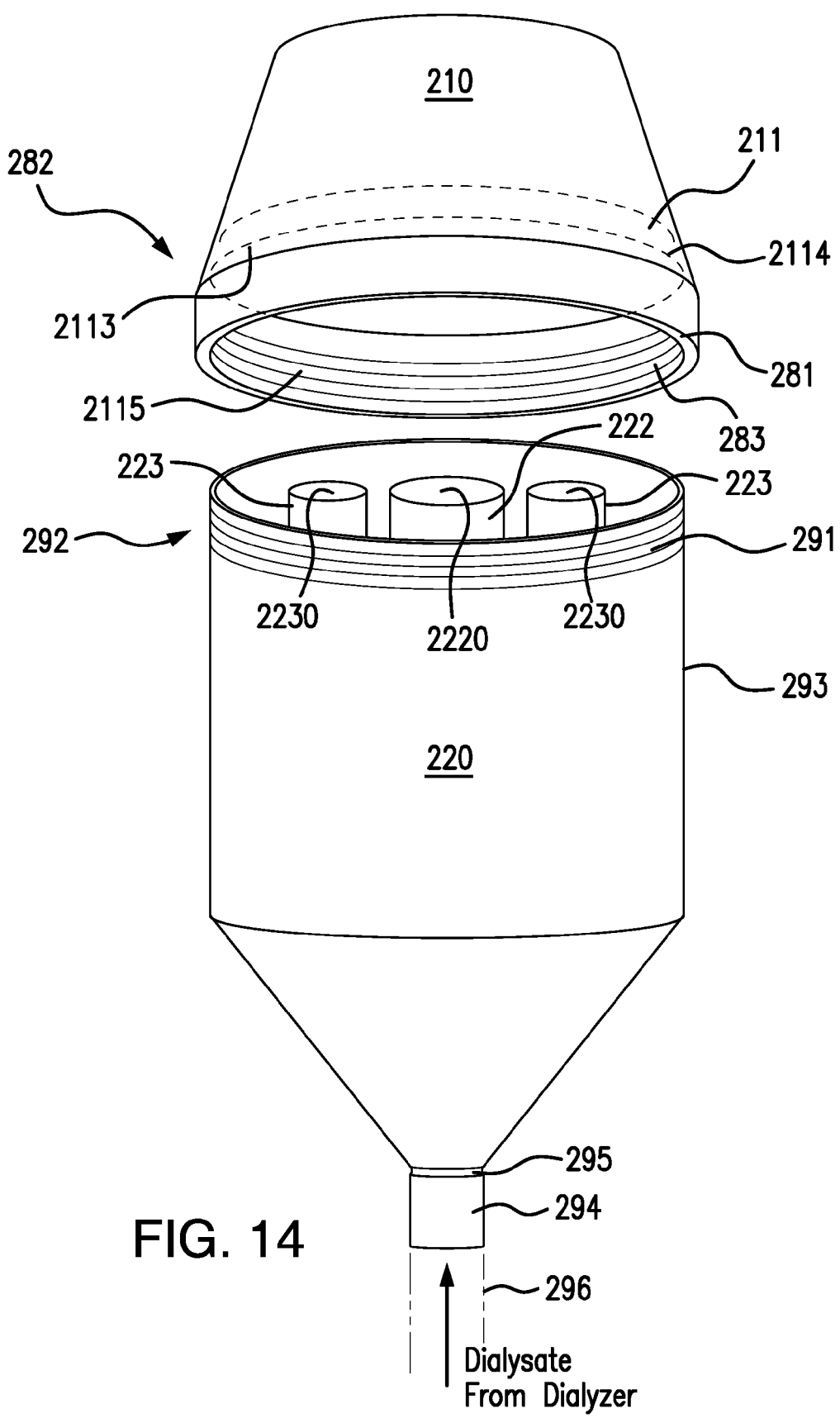
FIG. 14 is a perspective view of another manifold and sorbent cartridge mount configuration for making a releasable connection of these parts in a sorbent cartridge system according to an example of the present application.

Referring to FIG. 14, the lower face 2113 of bottom layer 211 of the sorbent bed in the sorbent cartridge 210 may have a liquid permeable membrane or layer 2114 exposed to top end 292 of the manifold 220 instead of providing a single or multiple fluid input ports at the bottom end of the sorbent cartridge. This configuration can permit inflow of dialysate fluid into the bottom layer 211 of the sorbent cartridge 210 where inputted from an adjacently positioned fluid discharge port of the manifold 220 while retaining solid particle content of the layer 211 in place therein. Referring further to FIG. 14 in this respect, as an option, the sorbent cartridge 210 may have a downward-extending collar or skirt 281 at its lower end 282 which has inner threading 283, such as helical threading, and defines a recess 2115, whilst the manifold 220 has matching external threading 291 on the upper end 292 of a housing or duct 293 thereof on which the inner threading 283 of the sorbent cartridge 210 can be screwed into a releasable fluid-tight connection between the two components. The manifold 220 can have peripheral discharge ports 2230 of low flow rate branches 223 and a central discharge port 2220 of a high flow rate branch 222 thereof, such as shown in previous FIGS. 5 and 7. 294 is a fitting, integral with or attachable to an inlet 295 of manifold 220, which can fluidly connect a dialysate line 296 supplied with spent dialysate from a dialyzer or other fluid supply line (not shown) to a main feeding passageway of the manifold (not shown here, e.g., see main branch 221 in FIG. 5). Fitting 294, if used, may be threaded and/or may be press fit (push fit) to the other mentioned parts. Valving and other additional elements not shown in this illustration may be included with the manifold. This connection strategy for the sorbent cartridge and manifold can be applied to any of the manifold configurations shown in FIGS. 5-11.

In an alternate option (not shown), the sorbent cartridge can be provided with external threading on the collar or skirt 281 at the lower end 282 of the cartridge and internal threading can be provided on the inner face of the housing or duct 293 at the upper end 292 of the manifold.

In another option (not shown), the bottom end of the sorbent cartridge and the top end of the manifold can be can be provided with at least one locking tab and at least one corresponding retainer flange on the opposing ends for releasably radially interlocking the ends of the parts in a fluid tight manner, such as using features adapted from U.S. Pat. No. 5,326,036, which is incorporated in its entirety by reference herein. Other attachments strategies for releasably attaching the sorbent cartridge and manifold may be used. For any of these examples, the intake manifold can be fixed in position on a dialysis machine and the sorbent cartridge can be detachably mountable to the intake manifold.

Figure 15:
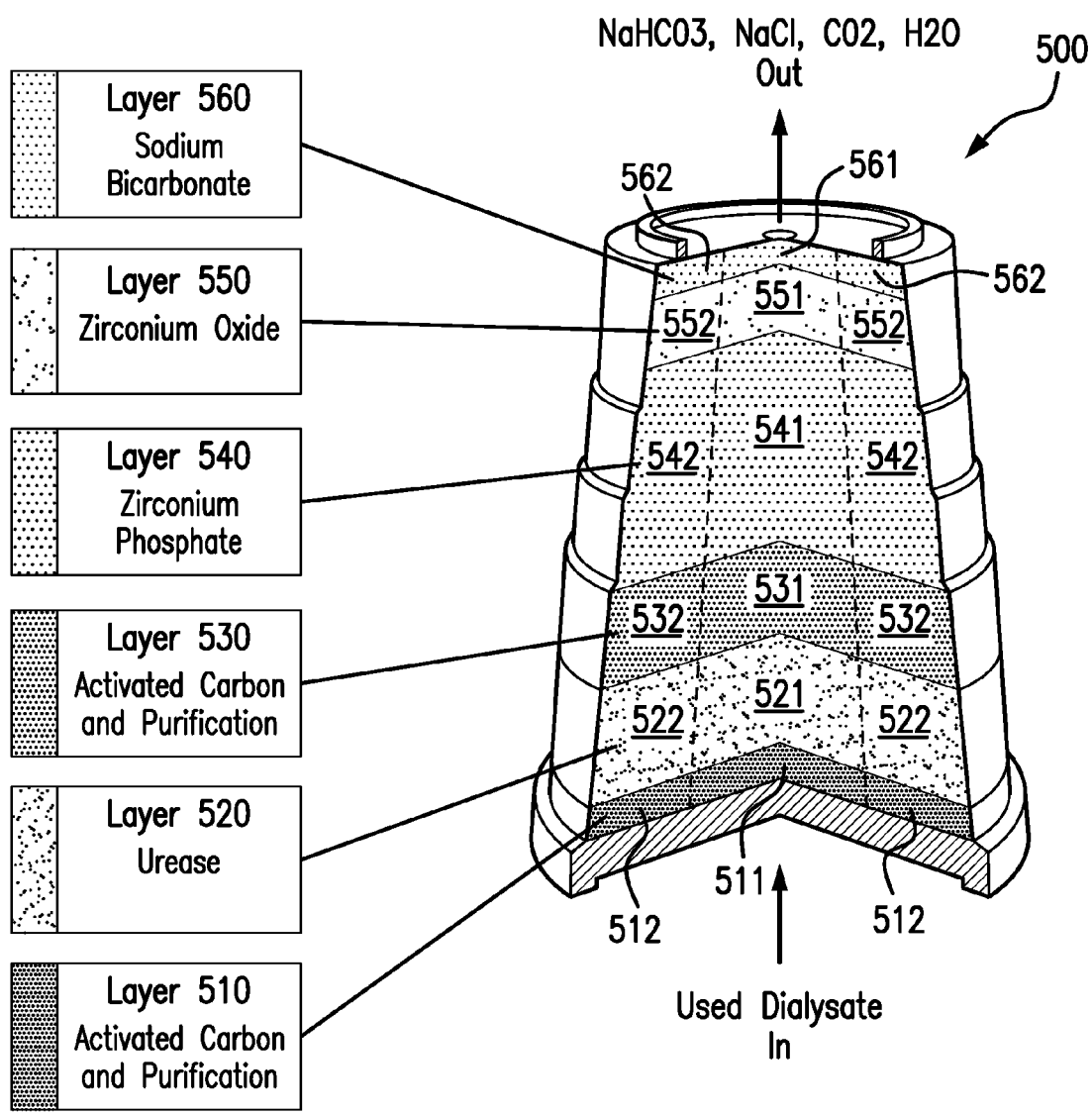
FIG. 15 is an exploded view of materials in one example of a sorbent cartridge which has multiple particle layers thereof which can be used in a sorbent cartridge system according to an example of the present application.

FIG. 15 is an exploded view of materials in one example of a sorbent cartridge, identified as cartridge 500, which can be used in combination with a manifold (not shown) in a sorbent cartridge system according to an example of the present application. Cartridge 500 includes an activated carbon layer 510, urease layer 520, activated carbon layer 530, zirconium phosphate layer 540, zirconium oxide layer 550, and sodium bicarbonate layer 560. These layers each form a distinct stratum of the overall particle bed. Additional, different, or less layers can be included in the sorbent bed in the cartridge. The zirconium oxide and sodium bicarbonate may be combined in a single layer. As shown in FIG. 15, the activated carbon layer 510 has a central region 511 and peripheral region 512, the urease layer 520 has a central region 521 and peripheral region 522, the activated carbon layer 530 has a central region 531 and peripheral region 532, the zirconium phosphate layer 540 has a central region 541 and peripheral region 542, the zirconium oxide layer 550 has a central region 551 and peripheral region 552, and the sodium bicarbonate layer 560 has a central region 561 and peripheral region 562. Each of the activated carbon layer 510, urease layer 520, activated carbon layer 530, zirconium phosphate layer 540, zirconium oxide layer 550, and sodium bicarbonate layer 560, can be provided with a central region and a peripheral region that have similar materials and packing densities thereof.

The flow rate differential concept described herein is not limited to the examples and kinds of cartridge layers and schemes of layers thereof shown in examples herein, and can be applied to other layers and schemes of sorbent cartridge layers, or other filter devices comprising different kinds of particle layers therein.

The sorbent cartridge(s) described here is/are preferably comprised of layers of highly specified and designed materials, and performs the regenerative function by employing three chemical phenomena: (i) adsorption, (ii) catalysis, and (iii) ion exchange. Adsorption describes the immobilization or fixation of mobile species at a solid interface or surface. Catalysis is a process by which the rate of a chemical reaction is increased by the reduction of the reaction activation energy via a component in the reaction whose net rate of consumption is zero. Ion exchange is a process in which particular solid materials adsorb species for which they have a high affinity and in turn release a species for which its affinity is lower.

In accordance with the techniques described herein, and with no limitation on the layer chemistry, a sorbent cartridge can be provided that can include a housing, a first sorbent layer, and a second sorbent layer and optionally one or more other layers. The housing can define a cartridge interior, the cartridge interior having a volume and configured to hold at least two layers of sorbent material. The housing can include a first end having a first port configured to permit entry of a fluid into the cartridge interior, and a second end distal to the first end and having a second port configured to permit exit of the fluid from the cartridge interior. One will appreciate that the techniques described herein need not be dependent on a particular housing or housing configuration, and that the housing is provided as a conventional way to hold and contain various sorbent layers, as well as effluent passing through the layers. The first sorbent layer can be situated in the cartridge interior. The first sorbent layer can have a first geometry and contain a first sorbent material. The second sorbent layer can be situated in the cartridge interior. The second sorbent layer can have a second geometry and can contain a second sorbent material. The first and second sorbent materials can have equivalent chemical compositions. The first geometry can differ from the second geometry in at least one dimension, or the first sorbent material can differ from the second sorbent material in at least one physical characteristic, or both.

The first and second geometries can differ from one another in one or more desired aspects. For example, the first geometry can differ from the second geometry with respect to size, shape, or both. The first sorbent layer can differ from the second sorbent layer in average height, average width, average length, or a combination thereof. The sorbent cartridge can have a central axis about which the first and second sorbent layers are centered, the first sorbent layer and the second sorbent layer can be cylindrical, or tapered in shape. The first geometry can differ from the second geometry with respect to average height, average radius, or both. The first sorbent layer and the second sorbent layer can differ in volume, weight, and/or density.

The first sorbent layer and the second sorbent layer can differ in surface area. This surface area difference can be achieved by any desired technique and/or configuration. For example, the volume of the first or second sorbent layer can be greater than the other.

Alternatively, or in addition, the size and/or shape of particles can differ between the first and second sorbent layers. The difference in particle size can be a difference in average particle size, whether, mean, median, or mode. Accordingly, the first and second sorbent materials can include particles and average particle size of the first sorbent material differs from average particle size of the second sorbent material. The first and second sorbent materials can include particles and at least one of the first and second sorbent materials can include a particle size not present in the other layer. The first and second sorbent materials can contain one or more particle sizes in common, but still different in average particle size. The first and second sorbent materials can include particles and at least one of the first and second sorbent materials can include a particle shape not present in the other layer. The first and second sorbent materials can contain one or more particle shapes in common, but still different with respect to one or more other particle shapes.

The first sorbent layer and the second sorbent layer can differ in sorbent capacity for at least one species targeted for absorption, adsorption, or both. This difference in sorbent capacity can be accomplished by any desired technique and/or configuration. The difference can be independent of chemistry and can instead be a result of one or more differences in volume, density, particle size, and/or particle shape. The first sorbent layer can have a greater sorbent capacity for at least one species targeted for absorption, adsorption, or both, compared to a sorbent capacity of the second sorbent layer for the at least one species, or vice versa.

The first and second sorbent layers can be positioned with respect to one another in any desired manner. For example, the first sorbent layer can be adjacent to the second sorbent layer. The first and second sorbent layer can be separated from one another by one or more additional layers. The first sorbent layer can be proximal to the first end and the second sorbent layer can be proximal to the second end, or vice versa. The first sorbent layer can at least partially surround the second sorbent layer, or vice versa. That is, a given stratum, cross-sectional volume, of the sorbent cartridge can contain one or more layers. Such layers can have chemical compositions, and the first geometry can differ from the second geometry in at least one dimension, the first sorbent material can differ from the second sorbent material in at least one physical characteristic, or both. For example, the sorbent cartridge can have at least one layer defined by a cross-sectional area with an inner region and outer region wherein the outer region surrounds the inner region, and the layer is defined by a height. The first and second sorbent layers can have the same average height with respect to an axial dimension between the first and second ends, and differ with respect to average width, average length, or both. The first and second sorbent layers can be concentric and positioned about a central axis along the axial dimension, the first sorbent layer having a width defined by a first radius extending from the central axis to the second sorbent layer, and the second sorbent layer having a width defined by the difference of the first radius and a second radius greater than the first radius. The sorbent layers can share a common axis, but have geometries that are not circular or even not curvilinear. For example, the geometries can be rectilinear. Circular or other curvilinear geometric layers need not share a common axis, and can be offset from one another with respect to a particular axis of the sorbent cartridge.

With respect to the difference between the first geometry and the second geometry, this difference with respect to size, shape, or both can be a difference of 5% or more, 10% or more, 15% or more, 20% or more, 50% or more, 100% or more, 200% or more, and the like. For instance, the difference can be from about 5% to about 200% with respect to size, shape, or both. Put another way, the comparison of the first sorbent layer and the second sorbent layer with respect to average height, average width, average length or any combination thereof can vary by these percents.

Further, with regard to comparing the first sorbent layer with the second sorbent layer with regard to volume, average density, particle size, (e.g., average particle size), and similar parameters, the difference between the first sorbent layer and the second sorbent layer can vary by these percents as set forth above.

The sorbent cartridge can include at least one additional sorbent layer including a sorbent material having a chemical composition differing from the chemical compositions of the first and second sorbent materials. The at least one additional sorbent layer can be located between the first end and first sorbent layer, between the first and second sorbent layers, or between the second sorbent layer and the second end. The first sorbent layer and the second sorbent layer can be separated from one another by at least one intervening layer including a third sorbent layer having a third geometry and including a third sorbent material, wherein the third sorbent material has a chemical composition non-equivalent to the chemical composition of the first and second sorbent layers. The first sorbent layer and the second sorbent layer can be separated from one another by at least one intervening layer including a third sorbent layer having a third geometry and include a third sorbent material. The first, second, and third sorbent materials can have equivalent chemical compositions, and the third geometry can differ from the first and second geometries, and/or the third sorbent material can differ from the first and second sorbent materials in at least one physical characteristic, and/or the third geometry can differ from either the first geometry or the second geometry as well as differing from either the first sorbent material or the second sorbent material in at least one physical property.

The first and second sorbent materials can have substantially the same or identical chemical compositions. The first and second sorbent materials can have equivalent chemical compositions. For example, the first and second sorbent material can both be cation exchangers, or can both be anion exchangers. The first and second sorbent materials can include at least one cation exchanger. The first and second sorbent materials can include the same cation exchanger. Any desired cation exchanger can be used. For example, the cation exchanger can include zirconium phosphate. The first and second sorbent layers can have the same cation exchange capacity, with respect to one or more types of cations. The first sorbent layer can have a greater cation exchange capacity than the second sorbent layer, or vice versa, with respect to one or more types of cations. The first and second sorbent materials can include at least one anion exchanger. The first and second sorbent materials can include the same anion exchanger. Any desired anion exchanger can be used. For example, the anion exchanger can contain hydrous zirconium oxide. The first and second sorbent layers can have the same anion exchange capacity with respect to one or more types of anion. The first sorbent layer can have a greater anion exchange capacity than the second sorbent layer, or vice versa, with respect to one or more types of anions.

The first and second sorbent materials can include urease, for example, in the form of a Jack Bean paste. The urease in the two different layers can be substantially the same or identical, and can be obtained from such sources as jack beans (for example, *Canavalia ensiformis*), yeasts, and bacteria (for example, *Bacillus pasteurii*). Any urease or combination of ureases can be employed. The urease can differ in specific activity between the two layers. The urease can differ in biological source. The urease can be isolated from a natural source or recombinant.

The first and second sorbent materials can include activated carbon. The activated carbon in the two layers can differ in the degree of activation, and/or both layers can contain non-activated carbon. The type of activated carbon in the two layers can be substantially the same or identical. The layers can share one or more types of activated carbon, but can differ with respect to one or more types of activated carbon. Any type or combination of types of activated carbon can be employed. The carbon can be chemically and/or physically activated. Any desired grade of activated carbon can be used. Examples of activated carbon include powdered activated carbon, granular activated carbon, bead activated carbon, extruded activated carbon, impregnated carbon, polymer-coated carbon, or any combination thereof. Activated carbon can differ with respect to porosity, specific surface area, and/or texture characteristics.

An embodiment described herein includes a sorbent cartridge having an inlet and outlet including at least a first layer and a second layer. The first layer and the second layer can contain particulate material having substantially the same or identical chemical composition. The first layer can be located closer to the inlet than the second layer. The particulate material in the first layer can have at least a greater/higher property then the particulate material in the second layer with respect to average particle size, average surface area, adsorption capacity, or any combination thereof for at least one species.

Non-limiting examples of sorbent cartridges are discussed as follows. Each of these examples can include a housing that surrounds all or a portion of the sorbent layers. The housing can conform to the shape of the sorbent layers in whole or part, or can be independent of the sorbent layer profile. Sorbent layers can be formed using any desired technique. For example, solid molds or hollow frames can be used to form the various strata (horizontal slices) and sorbent layers of a given sorbent cartridge. Sorbent layers of a given stratum can be formed simultaneously or in stages, for example, for successive concentric or nested sorbent layers. Adjacent sorbent layers can have sharp, distinct, blurred, and/or transitioned boundaries. Sorbent layers can contain gradients of sorbent material with respect to density, surface area, composition, and/or any other desired characteristic or combination of characteristics. The shape, size, order, and/or number of the strata and/or layers can vary as desired. Sorbent layers and/or strata can include any shapes or combination of shapes, curvilinear and/or rectilinear, for example, cones, cylinders, conical frustums, polygonal (regular and/or irregular) frustums, cylindrical prisms, conical prisms, polygonal (regular and/or irregular) prisms, and the like. The sides of a sorbent cartridge can be continuous or discontinuous, smooth or stepped, or a combination thereof; a description of one is understood to be representative of the other. Descriptions of square embodiments are also representative of rhombic, rectangular, regular polygonal, and irregular polygonal embodiments, and the like. Any two or more sorbent layers can have equivalent chemical compositions, but differ in respect to geometry and/or physical characteristic. While strata generally refer to horizontal slices, other orientations are also encompassed by the techniques described herein.

As an option, it is possible to prepare a layer or multiple layer arrangement and insert this arrangement into housing afterwards. The layer arrangement can be provided in a way that it can be inserted into a cartridge or housing or other holding structure at any time or right before using. The layer arrangement can be structurally kept in place by temporary molds (e.g., paper, plastic, and the like). The sorbent bed can include a multilayer stack which comprises at least the first and second layers, wherein the multilayer stack is insertable into a sorbent cartridge housing. All of the options, details, discussion above regarding the layers and the like equally apply here to this aspect of the present invention.

The techniques described herein, in part, can relate to a sorbent cartridge that includes at least dialysate treatment components of carbon, a urease source, zirconium phosphate ("ZP"), zirconium oxide, and (bi)carbonate.

The layers of materials in a cartridge of the present invention can be situated in the following preferred layer arrangement with these preferred materials from inlet to outlet:

Activated Carbon Layer (inlet)—adsorbs organic species, other lower polarity species such as oxidants and various heavy metal complexes emanating from both the water source and the patient.

Enzyme/Enzyme Retention Layer—the enzyme urease catalyzes the hydrolysis (hydrolytic decomposition) of aqueous urea to form bicarbonate and ammonium. The material used to retain or immobilize the urease can be alumina ($Al_2O_3$).

Activated Carbon Layer—performs same function as first carbon layer; in addition will adsorb organic species emanating from the enzyme source.

Zirconium Phosphate Layer—cation exchange material which adsorbs various cationic species in exchange for hydrogen and sodium ions.

Zirconium Oxide Layer—anion exchange material which adsorb various anionic species in exchange for chloride and hydroxide ions.

Sodium Bicarbonate Layer (outlet)—soluble sodium bicarbonate which dissolves upon priming the cartridge with dialysate thus increasing the concentration of sodium bicarbonate in the dialysate without directly pumping the sodium bicarbonate through the cartridge.

In sorbent dialysis, urea from the patient is transported into the dialysate at the dialyzer. Once in the dialysate, the urea is pumped to the sorbent cartridge where it is hydrolyzed into ammonium and bicarbonate ions. Due to this constant generation of bicarbonate in the dialysate for the duration of the dialysis treatment, the initial concentration of bicarbonate in the dialysate is typically lower in comparison to a normal single-pass dialysis treatment. This initial lower concentration prevents excessive bicarbonate in the dialysate as the treatment progresses, and thus prevents alkalosis. There are two features which have classically made this low initial bicarbonate paradigm safe: (1) a transient low concentration due to the dynamics of the system (not a constant, long duration exposure of low bicarbonate dialysate to a patient); and (2) the low volume ratio of dialysate to patient which inherently prevents the dialysate from driving the patient chemistries.

Compensation for this initial period of low dialysate bicarbonate in sorbent dialysis has classically involved the use of a large concentration of acetate ion donated by the sorbent cartridge which is transported to the patient (gradient driven) and converted to bicarbonate in the liver, thus preventing acidotic symptoms.

However, as an option there is no acetate in the sorbent cartridge. All of the buffer emanating from the cartridge is in the form of bicarbonate. Instead of the sorbent cartridge donating an initial bolus of acetate, the cartridge donates an initial bolus of sodium bicarbonate.

Cartridge designs according to the techniques described herein can provide bicarbonate initially to compensate for the period of lower bicarbonate and allows for a bicarbonate-only total buffer paradigm. Elimination of acetate from the cartridge, and thus the dialysate, a) simplifies the total buffer characterization, and/or b) eliminates potential complications due to acetate intolerance (high initial acetate concentrations coupled with new high flux/high flow rate dialysis), and/or c) eliminates potential alkalosis symptoms due to lack of understanding of the acetate-bicarbonate dynamic.

To reduce acetate, increase or maintain alkalinity, and/or reduce or control soluble Zr within tolerances, a series of layers can be used in the sorbent cartridge which includes a hydrous zirconium oxide layer of hydrous alkaline oxide-chloride that has an alkaline pH, and a (bi)carbonate layer, near or at the effluent outlet end of the cartridge.

A sorbent cartridge described herein can include a hydrous zirconium oxide layer that is hydrous zirconium oxide-chloride (HZO.Cl) having an alkaline pH. The formula for the HZO.Cl can be as in the Background above. To eliminate acetate, increase or maintain alkalinity, and/or reduce or control soluble zirconium within tolerances, HZO—Cl can be provided in the cartridge design. This HZO—Cl layer can be used without sodium zirconium carbonate. Alkaline pH of the HZO—Cl can reduce infused chloride or at least control it to a tolerable level, and can reduce soluble Zr discharge from the cartridge. Increasing alkaline pH can provide greater reductions in infused chloride, soluble Zr, or both. The HZO—Cl layer of alkaline pH can be used in combination with a (bi)carbonate layer that follows the hydrous zirconium oxide layer. The (bi)carbonate layer can comprise sodium carbonate ($Na_2CO_3$), sodium bicarbonate ($NaHCO_3$), or both, at the effluent end of the cartridge.

The hydrous zirconium oxide-chloride can have a pH greater than about 8, or greater than about 9, or about 9.5 to about 10.5, or about 10, or other alkaline values. The pH of the HZO—Cl generally increases with smaller relative proportions of chloride in the HZO—Cl. The chloride content in mg per g of HZO—Cl can be, for example, from about 25 mg/g to about 10 mg/g, or any amount that provides an alkaline pH.

With the cartridge design described herein, one or more further advantages, improvements, and/or properties can be achieved, especially compared to conventional cartridges. For example, it is possible to eliminate acetate content in the sorbent cartridge. In other words, the acetate content in the sorbent cartridge can be 0 wt % or about 0 wt % with respect to any layer and the entire sorbent cartridge. Additionally the sorbent cartridge has the ability to reduce unused material and operate with high dialysate flow rates and/or has the ability to operate with high flux dialyzers and thus have shorter treatment times (e.g., approximately four hours +/−30 minutes). For instance, dialysate flow rates can be from about 300 ml/min to about 500 ml/min with reduced unused material as compared to similar sorbent cartridges that lack a flow rate differential provided to one or more particle bed layers thereof. With the use of faster dialysis solution flow rates, this increases the efficiency of diffusion of urea from blood to dialysate. Further still, the techniques described herein have the ability to reduce TOC (total organic carbon) release to levels that are acceptable.

The order and composition of layers for a cartridge design of the present invention prior to be used to regenerate or purify spent dialysis fluid, can be, for example, as follows (e.g., top (exit or outlet) to bottom (entrance-inlet) in the cartridge):

a) one or more layers comprising, consisting essentially of, consisting of, or including sodium bicarbonate (e.g., 20 g to about 30 g), b) one or more layers comprising, consisting essentially of, consisting of, or including hydrous zirconium oxide-hydroxide and/or hydrous zirconium oxide-chloride (e.g., 150 g to about 250 g), c) one or more layers comprising, consisting essentially of, consisting of, or including zirconium phosphate (e.g., 650 g to about 1800 g), for instance, with a sodium loading of from about 50 mg to about 56 mg Na/g zirconium phosphate (the zirconium phosphate can have the formula as set forth in the Background above), d) one or more layers comprising, consisting essentially of, consisting of, or including a carbon layer or pad (e.g., about 50 g to about 500 g carbon), e) optionally one or more layers comprising, consisting essentially of, consisting of, or including alumina or other like material (e.g., about 100 g to about 500 g), f) one or more enzyme containing layers, such as a layer comprising, consisting essentially of, consisting of, or including urease, for example Jack Bean meal with or without alumina blend (e.g., about 100 g to about 400 g, including from about 5 grams to about 50 grams Jack Bean meal), and g) one or more layers comprising, consisting essentially of, consisting of, or including a carbon layer or pad (e.g., about 50 g to about 500 g carbon). These amounts for components a)-g) are provided as an example, and other amounts of these materials may be used.

The order and composition of layers for a cartridge design described herein after being used (or after a few minutes of being used) to regenerate or purify spent dialysis fluid, can be, for example, as follows (e.g., top (exit or outlet) to bottom (entrance-inlet) in the cartridge):

a) one or more layers comprising, consisting essentially of, consisting of, or including hydrous zirconium oxide-hydroxide and/or hydrous zirconium oxide-chloride (e.g., 150 g to about 250 g), b) one or more layers comprising, consisting essentially of, consisting of, or including zirconium phosphate (e.g., 650 g to about 1800 g), for instance, with a sodium loading of from about 50 mg to about 56 mg Na/g zirconium phosphate, c) one or more layers comprising, consisting essentially of, consisting of, or including a carbon layer or pad (e.g., about 50 g to about 500 g carbon), d) optionally one or more layers comprising, consisting essentially of, consisting of, or including alumina or other like material (e.g., about 100 g to about 500 g), e) one or more enzyme containing layers, such as a layer comprising, consisting essentially of, consisting of, or including urease, for example, Jack Bean meal with or without alumina blend (e.g., about 100 g to about 400 g, including from about 5 grams to about 50 grams Jack Bean meal), and f) one or more layers comprising, consisting essentially of, consisting of, or including a carbon layer or pad (about e.g., 50 g to about 500 g carbon). These amounts for components a)-g) are provided as an example, and other amounts of these materials may be used.

As indicated earlier the (bi)carbonate layer, after having spent or used dialysate fluid pass through the cartridge, will dissolve in the dialysate fluid, and disappear or essentially disappear from the cartridge as a layer.

Figure 16:
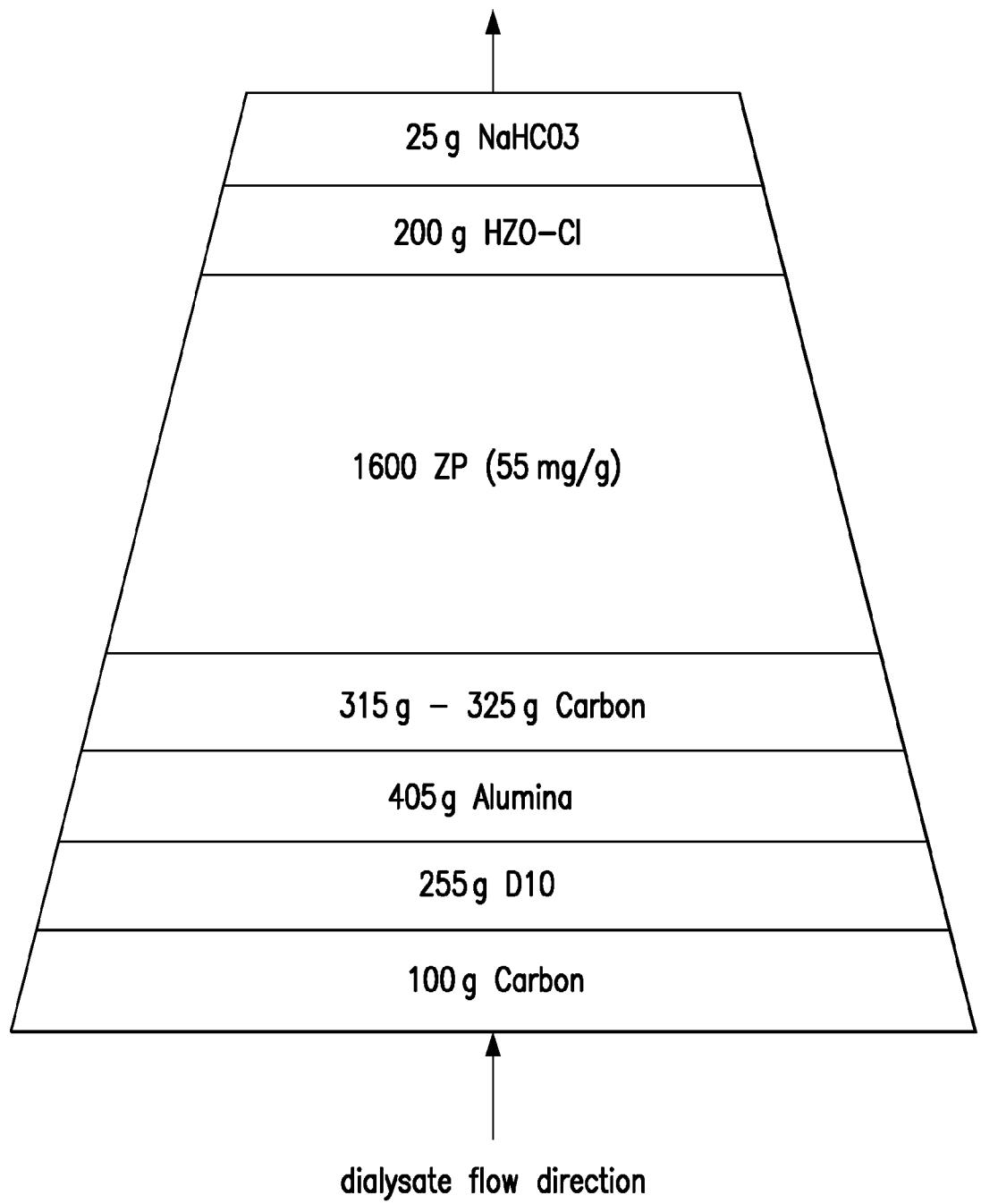
FIG. 16 is an exploded view of materials in a sorbent cartridge which can be used in a sorbent cartridge system according to an example of the present application.

Referring to FIG. 16, a sorbent cartridge which can be used in a sorbent cartridge system of the present invention can comprise a first carbon-containing layer(s), an enzyme-containing layer(s) ("D10") comprising Jack Bean meal that follows the first carbon-containing layer within the sorbent cartridge, an optional alumina layer(s), a second carbon-containing layer(s) that follows the enzyme-containing layer and alumina layer within the sorbent cartridge, a zirconium phosphate-containing layer(s), a hydrous zirconium oxide layer(s) that follows the zirconium phosphate-containing layer comprising hydrous zirconium oxide-chloride that has alkaline pH, and sodium (bi)carbonate layer(s) that follows the hydrous zirconium oxide layer.

In the example of the sorbent cartridge of FIG. 16, sodium (bi)carbonate can be used in an amount of from about 20 g to about 30 g, or from about 22 g to about 28 g, or from about 24 g to about 26 g, or about 25 g, or other amounts. The hydrous zirconium oxide-chloride which has an alkaline pH can be used in an amount of from about 50 g to about 300 g, or from about 75 g to about 200 g, or about 100 g, or other amounts. The zirconium phosphate layer can be used in an amount of from about 650 g to about 1800 g, or from about 800 g to about 1600 g, or from about 900 g to about 1300 g, or other amounts. The zirconium phosphate of this example can have a sodium loading of greater than 55 mg/g Na/g zirconium phosphate, or from about 56 mg to about 58 mg Na/g ZP, or about 57 mg Na/g ZP, or other values. The carbon layer or pad can be used in an amount of from about 50 g to about 500 g carbon or other amounts, the alumina or other like material can be used in an amount of from about 100 g to about 500 g or other amounts, the Jack Bean meal/alumina blend can be used in amounts of from about 100 g to about 400 g, including from about 5 grams to about 50 grams Jack Bean meal or other amounts, and the bottom carbon layer or pad can be used in an amount of from about 50 g to about 500 g carbon or other amounts. Any effective amounts of the above-described materials can be present in the cartridge. These amounts (or any amounts recited herein) can be with respect to a cartridge having the following dimensions: 2 inches-3 inches diameter by 5 inches to 10 inches length, or having the following dimensions: 4 inches-6 inches diameter by 6 inches-12 inches length. However, it is to be understood that these amounts provide weight ratios for each layer with respect to each other layer so as to permit adjustments in any sized cartridge.

A sorbent cartridge can include zirconium phosphate, such as (e.g. as a layer(s)) with increased sodium loading. To eliminate acetate, increase or maintain alkalinity, and/or reduce or control soluble zirconium within tolerances, HZO—Cl can be provided in the cartridge design. This HZO—Cl layer can be used without being combined with the SZC and glass beads. The chloride content of the HZO—Cl can be proportionally reduced sufficient to provide HZO—Cl of an alkaline pH. The hydrous zirconium oxide-chloride can have a pH greater than about 8, or greater than about 9, or about 9.5 to about 10.5, or about 10, or other alkaline values. The pH of the HZO—Cl generally increases with smaller relative proportions of chloride in the HZO—Cl. The chloride content in mg per g of HZO—Cl can be, for example, from about 25 mg/g to about 10 mg/g, or any amount that provides an alkaline pH. Alkalinity may be improved slightly by an increased sodium loading in the zirconium phosphate layer. Increasing alkaline pH can provide greater reductions in infused chloride, soluble Zr, or both. The HZO—Cl layer of alkaline pH can be used in combination with a (bi)carbonate layer that follows the hydrous zirconium oxide layer comprising sodium carbonate ($Na_2CO_3$), sodium bicarbonate ($NaHCO_3$), or both, at the effluent end of the cartridge.

The carbon can be activated carbon particles that are compacted into an activated carbon filter pad. The carbon can be activated carbon particles formed into layer of the particles that can be maintained in position by adjacent layers that adjoin the opposite sides of the carbon layer within the sorbent cartridge. Filter papers, diffusor pads, and separator rings (pads) which may be used, which can have conventional designs and structures for those types of sorbent cartridge components, such as those described in U.S. Patent Application Publication Nos. 2002/0112609 and 2012/0234762, which are incorporated in their entireties by reference herein. The various layers included in the sorbent cartridge usually are permeable to dialysate so that dialysate can continuously flow through the succession of different layers within the cartridge between the inlet and outlet thereof.

Any effective amounts of the above-described materials can be present in the cartridges described herein. For instance, with respect to the total weight of immobilized Jack Bean meal as a source of urease, the immobilized Jack Bean meal can be used in an amount of from about 100 grams to about 400 grams, or from about 150 grams to about 300 grams, or from about 200 grams to about 250 grams, or other amounts. As indicated, the Jack Bean meal can be immobilized, for example, by being blended with filler or the like such as alumina. Jack Bean meal is commercially available, such as from sources such as Sigma-Aldrich. Jack Bean meal can be used in the indicated immobilized form or by itself in amount of from about 5 grams to about 100 grams, or from about 8 grams to about 50 grams, or from about 10 grams to about 30 grams, or other amounts. Generally, the urease source, such as Jack Bean meal, can be present in an amount of from about 22,000 IU or less to about 55,000 IU or more, or from about 28,000 IU to about 42,000 IU. The particle size of the Jack Bean meal can be any effective size such as about 40 mesh or less (or less than about 0.4 mm). The remainder of the immobilized Jack bean meal can be alumina only or combinations of alumina and additional materials. Alumina is commercially available, such as from sources like Alcoa. Alumina can have the formula $Al_2O_3$. A particle size for alumina can be from about 20 microns to about 120 microns, or from about 20 microns to about 40 microns. The carbon in the carbon layers can be activated carbon in any amount and can be present in each carbon layer, for example, in an amount of from about 50 grams to about 500 grams, or from about 100 grams to about 400 grams, or from about 150 grams to about 300 grams, or from about 200 grams to about 250 grams, or from about 225 grams to about 275 grams, or other amounts. As indicated, the carbon can be activated carbon, such as activated granular carbon. The activated carbon is commercially available, such as from sources like Calgon. The activated carbon can have a particle size, for example, of from 0.4 to about 1.2 mm (or 12-50 mesh sieve), or other values. An alumina backup layer optionally can be present in an amount of from about 100 grams to about 500 grams, or from about 200 grams to about 400 grams, or from about 225 grams to about 300 grams, or other values. The particle size for the alumina in a backup layer can be the same as those indicated above for the immobilized Jack Bean meal layer.

As indicated, a sorbent cartridge described herein can be and preferably is acetate free or substantially acetate free. For example, the cartridge can contain less than about 3 wt % total acetate based on total weight of zirconium material and total acetate, or less than about 1 wt % total acetate based on total weight of zirconium material and total acetate, or less than about 0.5 wt % total acetate based on total weight of zirconium material and total acetate, or less than about 0.1 wt % total acetate based on total weight of zirconium material and total acetate, or from 0 to about 3 wt % total acetate based on total weight of zirconium material and total acetate, or from 0 to about 2 wt % total acetate based on total weight of zirconium material and total acetate, or from 0 to about 1 wt % total acetate based on total weight of zirconium material and total acetate, or from 0 to about 0.5 wt % total acetate based on total weight of zirconium material and total acetate, or other ranges within these values. These amounts of zirconium refer to all sources of zirconium in the cartridge, and they also can be applied to any individual layer of zirconium-containing material in the cartridge.

The hydrous zirconium oxide (HZO) component for the cartridges can have the formula $Zr(OH)_4 \cdot nH_2O$. As indicated, the cartridge design described herein can permit this material to be used in acetate-free form or essentially-acetate-free form. Acetate-free hydrous zirconium oxide (HZO) can be prepared, for example, by following the methods such as disclosed in U.S. Patent Application Publication Nos. US 2010/0078387 A1 and US 2006/0140840 A1, which are incorporated in their entirety by reference herein.

The zirconium phosphate can have an adsorption capacity for ammonia, $Ca^{2+}$, $Mg^{2+}$, $K^+$, and toxic heavy metals. As an option, the adsorption capacity of the zirconium phosphate can be approximately from about 20 mg $NH_4$—N/gm ZrP to about 45 mg or more $NH_4$—N/gm ZrP, and can be at least about 30 mg $NH_4$—N/gm ZrP; from about 2 mEq $Ca^{2+}$/gm ZrP to about 7 mEq $Ca^{2+}$/gm ZrP, and can be at least about 3 mEq $Ca^{2+}$/gm ZrP; from about 1 mEq $Mg^{2+}$/gm ZrP to about 5 mEq $Mg^{2+}$/gm ZrP, and can be at least about 2 mEq $Mg^{2+}$/gm ZrP; and from about 3 mEq HM/gm ZrP to about 9 mEq HM/gm ZrP, and can be at least about 6 mEq HM/gm ZrP for heavy metals (HM). Further, the zirconium phosphate can have a $Na^+$ content of from about 1.6 mEq $Na^+$/gm ZrP to about 2.7 mEq $Na^+$/gm ZrP, and can be about 2.2 mEq $Na^+$/gm and a pH of from about 5.5 to about 6. In the cartridge design, separate zirconium phosphate layers can be included which have different sodium content with respect to each other. Other pHs can be used and different $Na^+$ contents can be used with the understanding that reduced sodium loading can be used in the sorbent cartridges described herein. Also, the zirconium phosphate can have a minimum leachable $PO_4^{3-}$ for the material and can be less than about 0.05 mg $PO_4^{3-}$/gm ZrP. Other amounts can be used. In addition, the zirconium phosphate can have an average grain size of from about 30 to about 40 microns and has no residual sulfate or chloride (e.g., less than 0.01%). Other amounts can be used. Furthermore, the zirconium phosphate can satisfy the ANSI/AAMI RD-5-1992 standard on extractable toxic impurities and has a pH when in water of from about 6 to about 7. Further details of the zirconium phosphate and methods of making it, for example, are described in the indicated U.S. Pat. No. 6,627,164 B2, which is incorporated in its entirety by reference herein.

The zirconium phosphate can be used in any amount, subject to practical constraints of the size of the cartridge into which it may be loaded or positioned. As an option, the amount of the zirconium phosphate is a sufficient amount to remove at least partially if not substantially or entirely all of the ammonia present in the spent fluids while providing this performance with reduced sodium loading, such as compared to the indicated previous cartridge designs.

The cartridge can include with the bicarbonate layer, a second zirconium phosphate with higher sodium loading than a first one, and a hydrous zirconium oxide-hydroxide near the effluent outlet end of the cartridge. The sodium bicarbonate can be used in an amount of from about 20 g to about 30 g, or from about 22 g to about 28 g, or from about 24 g to about 26 g, or other amounts. The second zirconium phosphate layer can be used in an amount of from about 100 g to about 600 g, or from about 400 g to about 600 g, or from about 450 g to about 550 g, or other amounts. The second zirconium phosphate layer can have a sodium loading of from about 64 mg/g ZP to about 70 mg/g ZP, or from about 65 mg/g ZP to about 69 mg/g ZP, or from about 66 mg/g ZP to about 68 mg/g ZP, or other values. The hydrous zirconium oxide-hydroxide can be used in an amount of from about 150 g to about 250 g, or from about 175 g to about 225 g, or from about 190 g to about 200 g, or other amounts. The first zirconium phosphate layer can be used in an amount of from about 650 g to about 1600 g, or from about 800 g to about 1500 g, or from about 900 g to about 1300 g, or other amounts. The first zirconium phosphate layer can have a sodium loading of from about 50 mg/g ZP to about 56 mg/g ZP, or from about 51 mg/g ZP to about 55 mg/g ZP, or from about 52 mg/g ZP to about 54 mg/g ZP, or other values.

Other materials that can also be present in the sorbent cartridge include, but are not limited to, alumina, alumina supported urease, granulated activated carbon, activated alumina, zeolites, diatomaceous earth, direct urea sorbents, and other conventional adsorbent(s), fillers, glass beads, and the like. The materials, amounts, and other optional components and/or dialysis systems described in the following patents and publications can also be used in the present application and are incorporated in their entirety by reference herein and form a part of the present application: Des. 282,578; 3,669,878; 3,669,880; 3,697,410; 3,697,418; 3,703,959; 3,850,835; 3,989,622; 3,989,625; 4,025,608; 4,213,859; 4,256,718; 4,360,507; 4,460,555; 4,484,599; 4,495,129; 4,558,996; 7,033,498 B2, and the following articles, "Guide to Custom Dialysis," Product No. 306100-005, Revision E, pages 1-54, dated September 1993 and "Sorbent Dialysis Primer," Product No. 306100-006, Edition 4, pp. 1-51, dated September 1993 of Cobe Renal Care, Inc.

A single cartridge can be used which combines all of the above-described materials. In another example, a series of cartridges can be used wherein the combination of the above-described materials can be present in one or more cartridges. For instance, urease, alumina, and split carbon layers that sandwich these two layers can be provided in a first cartridge and the remaining layers can be placed in a second cartridge, and so on. Optionally, these various indicated layers in these sequences can be divided over three different cartridges or more. As indicated, all of the materials can be provided in a single cartridge and can be arranged as distinct layers in the single cartridge. As an option, a cartridge layer can be composed of at least about 50% by weight, or at least 75% by weight, or at least about 80% by weight, or at least about 90% by weight, or at least about 95% by weight, or least about 99% by weight, or up to 100% by weight, or from about 50% to about 100% by weight, or from about 75% to about 100% by weight, or from about 90% to about 100% by weight, or from about 95% to about 100% by weight, or from about 99% to about 100% by weight, of only the material or materials indicated for use in that layer.

As an option, in addition to any carbon filter pad that may be used in providing one or both of the indicated carbon layers on each side of the enzyme containing layer, one or more filter pads can be located throughout the sorbent cartridge to ensure that the layer integrity is maintained during operation. The filter pad can be made of any type of material, for instance, standard filter paper or cellulose pads and the like and typically is the diameter or length-width of the cartridge in order to separate completely one layer from another layer. A flow diffuser which uniformly diffuses the used dialysate throughout the entire width or diameter of the sorbent cartridge can be used. The flow diffuser can have a design of radial spreading channels made of plastic or other suitable materials. The flow diffuser is typically located prior to any of the optional filter pads or materials used in the sorbent cartridge and is adjacent to the inlet (or part of the inlet) of the sorbent cartridge. A barrier layer(s) can also be used in the sorbent cartridge. A barrier layer can be located between the immobilized enzyme layer and the alumina layer, if present. An example of a barrier layer includes filter paper and the like.

Various overall shapes of the sorbent cartridge include, but are not limited to, a cylindrical shape, rectangular shape, a pyramidal-cylindrical (stepped) shape as shown, for instance, in FIG. 1 and so on. The shape can be straight-edged or tapered, and so on. Any geometric shape can generally be used. As an option, the PD cartridge has the following dimensions: 2 inches-3 inches diameter by 5 inches to 10 inches length. The HD cartridge can have the following dimensions: 4 inches-6 inches diameter by 6 inches-12 inches long. Other dimensions can be used depending on the needs of the purifying, amount to purify, operating system and the like. Examples of cartridge designs are further shown in U.S. Pat. No. 6,878,283, which is incorporated in its entirety by reference herein. Examples of cartridges are also described in one or more of the patents and/or publications identified herein.

In preparing the Jack Bean meal, the Jack Bean meal can be extracted with a liquid organic solvent, and then the solvent can be evaporated to eliminate organic impurities with the volatiles, and leave intact active urease in the non-evaporated Jack Bean meal residue. The extraction solvent can be, for example, a C1-C4 lower alkyl alcohol such as ethanol, methanol, (iso)propanol, and (iso)butanol, or other liquid organic solvents. Jack Bean meal can be dissolved in ethanol, for example, and then the ethanol can be evaporated to eliminate organic impurities with the volatized fraction and leave an organic, oily residue which contains urease and various higher molecular weight fatty acid derivatives. The evaporation can be promoted by application of heat sufficient to increase volatization without denaturing the urease. The residue can be dried at any temperatures that do not denature the urease, and the resulting dried residue can be used as a purified source of Jack Bean meal and urease remaining therein in a sorbent cartridge, such as an indicated design herein.

As another pretreatment of Jack Bean meal that can be used according to the techniques described herein, urease can be extracted from Jack Bean meal by an extraction process and then the urease can be isolated and lyophilized before incorporation into a sorbent cartridge. Methods for extracting urease from Jack Bean meal can be adapted from known methods in this respect, and the urease extracts can be lyophilized and used in sorbent cartridges. For example, urease may be extracted from Jack Bean meal through steps including solvent extraction, heat treatment, acid precipitation, and lyophilization. The extraction process may be repeated to increase purity of the urease extract product. For extraction of urease, for example, Jack Bean meal may be mixed with acetone and stirred at about room temperature for one or more minutes. The resulting material can be heated to remove cloudy materials, and urease can be precipitated in the remaining supernatant by adjusting the pH of the solution with acid. The acid precipitated urease can be neutralized to a suitable pH, and then lyophilized before use in a sorbent cartridge.

The cartridges as described herein can be used in a variety of separation systems and can be used in the regeneration or purification of dialysates (e.g., HD) or PD solutions. In a less complicated design, spent or used dialysate or PD solutions can simply be passed through one or more cartridges to purify or regenerate the spent fluids. Such a system can be straightforward in setup and can involve merely using a column-type setup wherein the spent fluids are passed from top to bottom wherein gravity permits the spent fluid to go through the cartridge or spent fluid can be passed through the cartridge under pressure which permits the spent fluids to be introduced in any direction. In a more specific system, the system set forth in FIG. 17, and identified by numeral 600, can be adapted to use an indicated sorbent cartridge as used especially for hemodialysis; that is a system that can be used as a closed system, or alternatively in a single pass dialysis system (not shown). Such a system permits the continuous reusing of the regenerated dialysate in a patient during dialysis treatment. With respect to a single pass system (not shown), in lieu of discarding the used dialysate to a floor drain, as an alternative, the used dialysis can simply be collected in a container which then can be regenerated or purified by passing the spent dialysate through one or more cartridges as described above.

With respect to peritoneal dialysis, there are several options. First, like hemodialysis, the peritoneal dialysis solution that is spent can be directly passed through one or more cartridges to purify or regenerate the used peritoneal dialysis solution in order to remove the waste products. Alternatively, the peritoneal dialysis solution which is used or spent can first be passed through a dialyzer in the same manner as blood during hemodialysis wherein dialysate removes waste products and the like from the peritoneal dialysis solution and then the dialysate can be regenerated or purified by passing the used or spent dialysate through the cartridge. Either system can be used. With a closed PD system, the risk of peritonitis can be reduced since the frequent connections made with conventional systems between the catheter in the peritoneal cavity and a succession of dialysis solution containers can be avoided.

Figure 17:
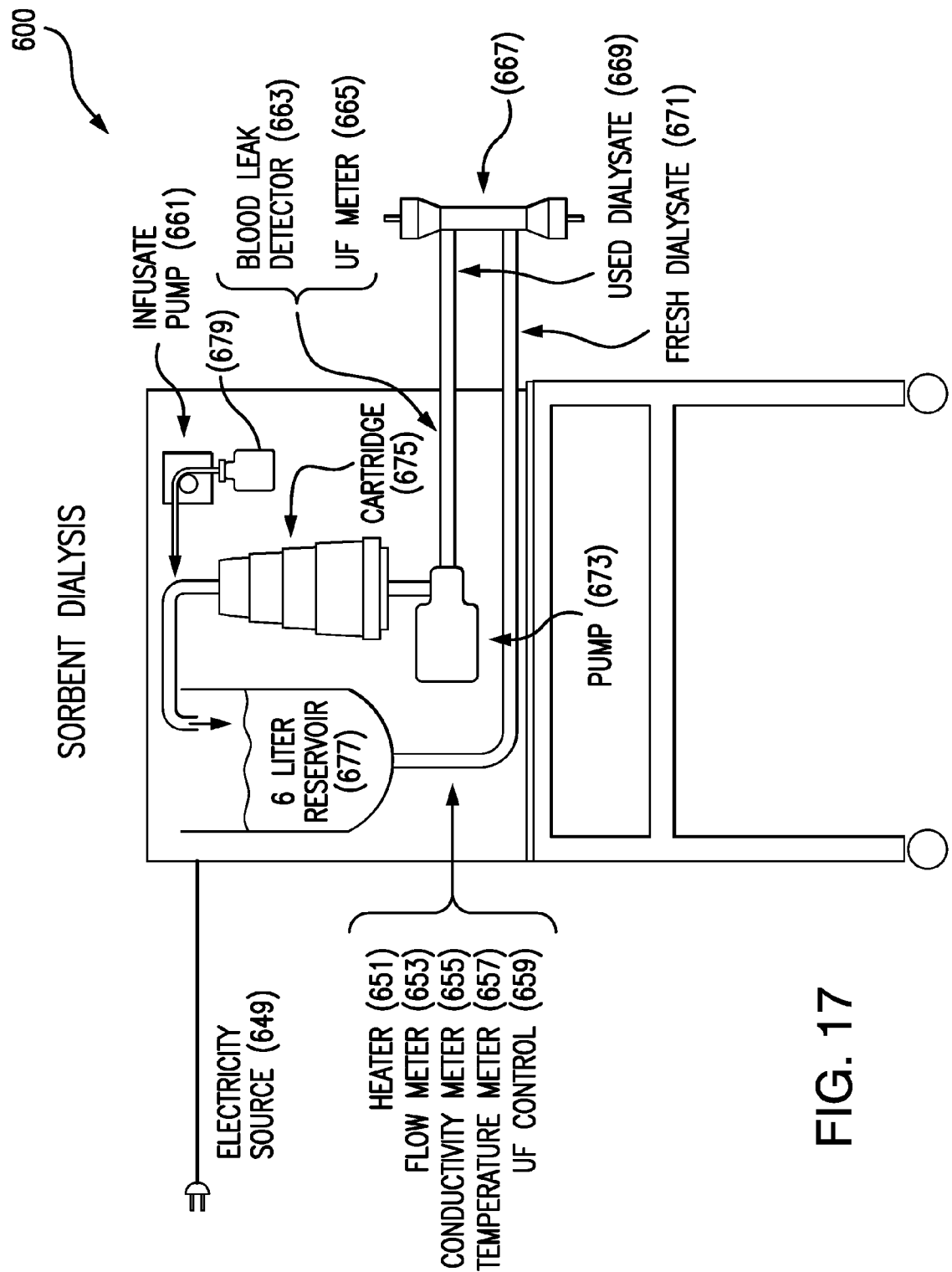
FIG. 17 is a schematic diagram showing a sorbent dialysis system which includes a sorbent cartridge system according to an example of the present application.

Referring to FIG. 17, 675 refers to a cartridge system, which is a cartridge system of the present application (i.e., a combination of the sorbent cartridge and intake manifold). 649 refers to a source of electricity to operate the dialysis system. 651 represents a heater, 653 represents a flow meter, 655 represents a conductivity meter, 657 represents a temperature meter, and 659 represents a UF control. These items are conventional items in a sorbent dialysis system and are known to those skilled in the art and can be used in implementing the techniques described herein. 661 is an infusate pump that is used to pump in fresh concentrate 679 to be mixed with the regenerated dialysate which ultimately enters the reservoir 677 which can be a six liter reservoir. 663 represents a blood leak detector and 665 represents a UF meter which are conventional items in dialysis systems and can be used herein. Component 667 represents a dialyzer. As indicated, a dialyzer is known by those skilled in the art and typically is a system or component that contains a membrane in order to have the waste products pass through the membrane to the dialysate fluid. Similarly, 669 represents used dialysis leaving the dialyzer and 671 represents fresh dialysate entering the dialyzer 667. Component 673 is a pump to pump the used dialysate from the dialyzer into the cartridge system 675 which are the cartridges of the present application.

The sorbent cartridges described herein can be made for use in multiple hours of dialysis treatment, such as, for example, for up to about 4 hours of dialysis treatment or for up to about 8 hours of dialysis treatment. For example, the 8 hour cartridges can typically be made for home use and the 4 hour cartridges can typically be made for dialysis treatment in medical treatment or dialysis centers. The cartridges described herein can generally be used with any type of dialysis system as described above. The flows that pass through the cartridge are typically any conventional flows. For instance, flows from about 50 ml/min or less to 500 ml/min or more of dialysate can flow through the cartridge and can be used in the systems described herein. Other flows can be used depending upon the size of the cartridge and the operating system.

The dialysis systems or components thereof described in the above and following patents can be used in the present application and these systems can incorporate the materials and/or cartridges described herein: U.S. Pat. Nos. 7,033,498 B2; 8,663,463; 8,597,505; 8,580,112; 8,500,994; 8,366,921; 8,343,346; 8,475,399; and 8,012,118; and U.S. patent application Ser. No. 14/656,729 filed Mar. 13, 2015. All of these patents and patent applications are incorporated in their entirety by reference herein and form a part of the present application.

There are numerous uses for the materials described herein and especially the cartridges described hereinsuch as the regeneration of dialysis fluids as mentioned above. Furthermore, the cartridges can also be used in any separation process which requires the removal of impurities or waste products from a fluid or other medium that is passable through the materials of the present invention. Also, the techniques described herein may be useful with respect to treating drug overdose patients or other patients which are in need or removing undesirable or dangerous contaminants in a person's blood stream.

Accordingly, the techniques described herein provide useful embodiments that allow the regeneration of dialysate type fluids and other fluids.

The techniques described herein can be used to provide stationary sorbent dialysis systems or portable sorbent dialysis systems. The sorbent dialysis systems can include sorbent hemodialysis, a wearable artificial kidney, sorbent peritoneal dialysis, and other sorbent dialysis systems.

The techniques described herein include the following aspects/embodiments/features in any order and/or in any combination:

1. The present invention relates to a sorbent cartridge system, comprising:
    a sorbent cartridge comprising i) a continuous sidewall extending between a fluid inlet and a fluid outlet, which define a chamber, ii) at least one layer comprising solid particulate media, wherein the at least one layer extends across the chamber within the continuous sidewall, and the at least one layer comprises a first region and a second region adjacent the first region and located closer to the continuous sidewall than the first region; and
    an intake manifold comprising at least one first discharge port and at least one second fluid discharge port, wherein the intake manifold and sorbent cartridge are positionable with respect to each other to locate the first region of the sorbent cartridge for fluid communication with the at least one first discharge port and locate the second region of the sorbent cartridge for fluid communication with the at least one second fluid discharge port, wherein the intake manifold is configured wherein a first volumetric flow rate of fluid discharged at the first fluid discharge port into the first region is greater as compared to a second volumetric flow rate of fluid discharged at the second fluid discharge port into the second region.
2. The sorbent cartridge system of any preceding or following embodiment/feature/aspect, wherein the intake manifold comprises i) at least one central branch passageway comprising a first hydraulic diameter and the at least one first discharge port, ii) at least one peripheral branch passageway comprising a second hydraulic diameter and the at least one second discharge port, and iii) a fluid feeding passageway for supplying fluid concurrently to the at least one central branch passageway and the at least one peripheral branch passageway, wherein the first hydraulic diameter of the at least one central branch passageway is greater than the second hydraulic diameter of the at least one peripheral branch passageway.
3. The sorbent cartridge system of any preceding or following embodiment/feature/aspect, wherein the at least one peripheral branch passageway comprises a plurality of pipes having discharge openings arranged in spaced-apart pattern around the at least one discharge port of the at least one central branch passageway, wherein each of the plurality of pipes having the second hydraulic diameter.
4. The sorbent cartridge system of any preceding or following embodiment/feature/aspect, wherein the at least one peripheral branch passageway comprises a single duct having a continuous discharge opening which is arranged around and radially spaced from the at least one discharge port of the at least one central branch passageway, wherein the single duct having the second hydraulic diameter.
5. The sorbent cartridge system of any preceding or following embodiment/feature/aspect, wherein the intake manifold comprises concentric tubes comprising i) an inner tube comprising a first hydraulic diameter, the at least one first discharge port, and at least one first fluid supply inlet port, ii) an outer tube concentrically surrounding the inner tube, wherein the outer tube comprising a second hydraulic diameter, the at least one second discharge port, and at least one second fluid supply inlet port, iii) a fluid feeding passageway for supplying fluid concurrently to the at least one first fluid supply inlet port of the inner tube and the at least one second fluid supply inlet port of the outer tube, wherein the first hydraulic diameter of the inner tube is greater than the second hydraulic diameter of the outer tube.
6. The sorbent cartridge system of any preceding or following embodiment/feature/aspect, wherein the intake manifold comprises a spray nozzle head comprising i) a housing defining a fluid chamber which is fluidly linkable with a fluid supply line and an open side, and ii) a perforated plate covering the open side of the housing, wherein the perforated plate comprises (a) a first central region comprising a first perforated plate portion defining a plurality of first holes passing through a first solid plate portion, wherein the first holes have a first diameter, and (b) a second peripheral region which surrounds the first central region, wherein the second peripheral region comprising a second perforated plate portion defining a plurality of second holes passing through a second solid plate portion, wherein the second holes have a second diameter, and wherein the first diameter of the first holes are larger than the second diameter of the second holes, and the at least one first discharge port comprises the first holes and the at least one second discharge port comprises the second holes.
7. The sorbent cartridge system of any preceding or following embodiment/feature/aspect, wherein the intake manifold is configured wherein the first volumetric flow rate of fluid discharged at the first fluid discharge port into the first region is at least 5% greater as compared to the second volumetric flow rate of fluid discharged at the second fluid discharge port into the second region.
8. The sorbent cartridge system of any preceding or following embodiment/feature/aspect, wherein the intake manifold is configured wherein the first volumetric flow rate of fluid discharged at the first fluid discharge port into the first region is at least 10% greater as compared to the second volumetric flow rate of fluid discharged at the second fluid discharge port into the second region.
9. The sorbent cartridge system of any preceding or following embodiment/feature/aspect, wherein the first region comprises first solid particulate media having a first average packing density, and the second region comprises second solid particulate media having a second average packing density, wherein the first average packing density is within ±1% of the second average packing density (e.g., when at least the first and second layers are wet, such as uniformly wet).
10. The sorbent cartridge system of any preceding or following embodiment/feature/aspect, wherein the sorbent cartridge and the intake manifold are detachably mountable to each other.
11. The sorbent cartridge system of any preceding or following embodiment/feature/aspect, wherein the intake manifold is fixed in position on a dialysis machine and the sorbent cartridge is detachably mountable to the intake manifold.

12. The sorbent cartridge system of any preceding or following embodiment/feature/aspect, wherein the sorbent cartridge comprises an enzyme-comprising layer, and a zirconium phosphate-containing layer that follows the enzyme-comprising layer within the sorbent cartridge, wherein the zirconium phosphate-containing layer is the at least one layer comprising solid particulate media.

13. The sorbent cartridge system of any preceding or following embodiment/feature/aspect, wherein the sorbent cartridge further comprising, from the fluid inlet to the fluid outlet:
   a) a first carbon-containing layer that precedes the enzyme-comprising layer;
   b) the enzyme-comprising layer, which follows the first carbon-containing layer within the sorbent cartridge;
   c) a second carbon-containing layer that follows the enzyme-comprising layer within the sorbent cartridge;
   d) the zirconium phosphate-containing layer, which follows the second carbon-containing layer within the sorbent cartridge;
   e) a hydrous zirconium oxide layer that follows the zirconium phosphate-containing layer comprising hydrous zirconium oxide-chloride having an alkaline pH; and
   f) a (bi)carbonate layer that follows the hydrous zirconium oxide layer comprising sodium (bi)carbonate.

14. The present invention relates to a method to regenerate or purify spent dialysis fluid comprising passing spent dialysis fluid through a sorbent cartridge system of any preceding or following embodiment/feature/aspect.

15. The method of any preceding or following embodiment/feature/aspect, wherein the dialysis fluid is passed through the sorbent cartridge system for a treatment session having a duration of 180 minutes to 300 minutes, wherein the dialysis fluid flows concurrently through the first region at a first fluid flow rate and through the second region at a second fluid flow rate, wherein the first fluid flow rate is at least 5% more than the second fluid flow rate for at least 90% of the treatment session.

16. The method of any preceding or following embodiment/feature/aspect, wherein the dialysis fluid is passed through the sorbent cartridge system for a treatment session having a duration of 180 minutes to 300 minutes, wherein the dialysis fluid flows concurrently through the first region at a first fluid flow rate and through the second region at a second fluid flow rate, wherein the first fluid flow rate is at least 10% more than the second fluid flow rate for 100% of the treatment session.

17. The method of any preceding or following embodiment/feature/aspect, wherein the dialysis fluid is passed through the sorbent cartridge system for a treatment session having a duration of 180 minutes to 300 minutes, wherein the dialysis fluid flows concurrently through the first region at a first fluid flow rate and through the second region at a second fluid flow rate, wherein the first fluid flow rate is at least 15% more than the second fluid flow rate for at least 90% of the treatment session.

18. The present invention relates to a dialysis system to regenerate or purify spent dialysis fluid comprising the sorbent cartridge system of any preceding or following embodiment/feature/aspect.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It will be apparent to those skilled in the art that various modifications and variations can be made to the embodiments of the present invention without departing from the spirit or scope of the present invention. Thus, it is intended that the present invention covers other modifications and variations of this invention provided they come within the scope of the appended claims and their equivalents.

What is claimed is:

1. A sorbent cartridge system, comprising:
   a sorbent cartridge comprising i) a continuous sidewall extending between a fluid inlet and a fluid outlet, which define a chamber, ii) at least one layer comprising solid particulate media, wherein the at least one layer extends across the chamber within the continuous sidewall, and the at least one layer comprises a first region and a second region adjacent the first region and located closer to the continuous sidewall than the first region; and
   an intake manifold comprising at least one first discharge port and at least one second fluid discharge port, wherein the intake manifold and sorbent cartridge are positionable with respect to each other to locate the first region of the sorbent cartridge for fluid communication with the at least one first discharge port and locate the second region of the sorbent cartridge for fluid communication with the at least one second fluid discharge port, wherein the intake manifold is configured wherein a first volumetric flow rate of fluid discharged at the first fluid discharge port into the first region is greater as compared to a second volumetric flow rate of fluid discharged at the second fluid discharge port into the second region,
   wherein the intake manifold comprises i) at least one central branch passageway comprising a first hydraulic diameter and the at least one first discharge port, ii) at least one peripheral branch passageway comprising a second hydraulic diameter and the at least one second discharge port, and iii) a fluid feeding passageway for supplying fluid concurrently to the at least one central branch passageway and the at least one peripheral branch passageway, wherein the first hydraulic diameter of the at least one central branch passageway is greater than the second hydraulic diameter of the at least one peripheral branch passageway.

2. The system of claim 1, wherein the at least one peripheral branch passageway comprises a plurality of pipes having discharge openings arranged in spaced-apart pattern around the at least one discharge port of the at least one central branch passageway, wherein each of the plurality of pipes having the second hydraulic diameter.

3. The system of claim 1, wherein the at least one peripheral branch passageway comprises a single duct having a continuous discharge opening which is arranged around and radially spaced from the at least one discharge port of the at least one central branch passageway, wherein the single duct having the second hydraulic diameter.

4. A sorbent cartridge system, comprising:
a sorbent cartridge comprising i) a continuous sidewall extending between a fluid inlet and a fluid outlet, which define a chamber, ii) at least one layer comprising solid particulate media, wherein the at least one layer extends across the chamber within the continuous sidewall, and the at least one layer comprises a first region and a second region adjacent the first region and located closer to the continuous sidewall than the first region; and
an intake manifold comprising at least one first discharge port and at least one second fluid discharge port, wherein the intake manifold and sorbent cartridge are positionable with respect to each other to locate the first region of the sorbent cartridge for fluid communication with the at least one first discharge port and locate the second region of the sorbent cartridge for fluid communication with the at least one second fluid discharge port, wherein the intake manifold is configured wherein a first volumetric flow rate of fluid discharged at the first fluid discharge port into the first region is greater as compared to a second volumetric flow rate of fluid discharged at the second fluid discharge port into the second region, wherein the intake manifold comprises concentric tubes comprising i) an inner tube comprising a first hydraulic diameter, the at least one first discharge port, and at least one first fluid supply inlet port, ii) an outer tube concentrically surrounding the inner tube, wherein the outer tube comprising a second hydraulic diameter, the at least one second discharge port, and at least one second fluid supply inlet port, iii) a fluid feeding passageway for supplying fluid concurrently to the at least one first fluid supply inlet port of the inner tube and the at least one second fluid supply inlet port of the outer tube, wherein the first hydraulic diameter of the inner tube is greater than the second hydraulic diameter of the outer tube.

5. A sorbent cartridge system, comprising:
a sorbent cartridge comprising i) a continuous sidewall extending between a fluid inlet and a fluid outlet, which define a chamber, ii) at least one layer comprising solid particulate media, wherein the at least one layer extends across the chamber within the continuous sidewall, and the at least one layer comprises a first region and a second region adjacent the first region and located closer to the continuous sidewall than the first region; and
an intake manifold comprising at least one first discharge port and at least one second fluid discharge port, wherein the intake manifold and sorbent cartridge are positionable with respect to each other to locate the first region of the sorbent cartridge for fluid communication with the at least one first discharge port and locate the second region of the sorbent cartridge for fluid communication with the at least one second fluid discharge port, wherein the intake manifold is configured wherein a first volumetric flow rate of fluid discharged at the first fluid discharge port into the first region is greater as compared to a second volumetric flow rate of fluid discharged at the second fluid discharge port into the second region, wherein the intake manifold comprises a spray nozzle head comprising i) a housing defining a fluid chamber which is fluidly linkable with a fluid supply line and an open side, and ii) a perforated plate covering the open side of the housing, wherein the perforated plate comprises (a) a first central region comprising a first perforated plate portion defining a plurality of first holes passing through a first solid plate portion, wherein the first holes have a first diameter, and (b) a second peripheral region which surrounds the first central region, wherein the second peripheral region comprising a second perforated plate portion defining a plurality of second holes passing through a second solid plate portion, wherein the second holes have a second diameter, and wherein the first diameter of the first holes are larger than the second diameter of the second holes, and the at least one first discharge port comprises the first holes and the at least one second discharge port comprises the second holes.

6. The system of claim 1, wherein the intake manifold is configured wherein the first volumetric flow rate of fluid discharged at the first fluid discharge port into the first region is at least 5% greater as compared to the second volumetric flow rate of fluid discharged at the second fluid discharge port into the second region.

7. The system of claim 1, wherein the intake manifold is configured wherein the first volumetric flow rate of fluid discharged at the first fluid discharge port into the first region is at least 10% greater as compared to the second volumetric flow rate of fluid discharged at the second fluid discharge port into the second region.

8. The system of claim 1, wherein the first region comprises first solid particulate media having a first average packing density, and the second region comprises second solid particulate media having a second average packing density, wherein the first average packing density is within ±1% of the second average packing density.

9. The system of claim 1, wherein the sorbent cartridge and the intake manifold are detachably mountable to each other.

10. The system of claim 1, wherein the intake manifold is fixed in position on a dialysis machine and the sorbent cartridge is detachably mountable to the intake manifold.

11. The system of claim 1, wherein the sorbent cartridge comprises an enzyme-comprising layer, and a zirconium phosphate-containing layer that follows the enzyme-comprising layer within the sorbent cartridge, wherein the zirconium phosphate-containing layer is the at least one layer comprising solid particulate media.

12. The system of claim 11, wherein the sorbent cartridge further comprising, from the fluid inlet to the fluid outlet:
a) a first carbon-containing layer that precedes the enzyme-comprising layer;
b) the enzyme-comprising layer, which follows the first carbon-containing layer within the sorbent cartridge;
c) a second carbon-containing layer that follows the enzyme-comprising layer within the sorbent cartridge;
d) the zirconium phosphate-containing layer, which follows the second carbon-containing layer within the sorbent cartridge;
e) a hydrous zirconium oxide layer that follows the zirconium phosphate-containing layer comprising hydrous zirconium oxide-chloride having an alkaline pH; and
f) a (bi)carbonate layer that follows the hydrous zirconium oxide layer comprising sodium (bi)carbonate.

13. A method to regenerate or purify dialysis fluid comprising passing dialysis fluid through a sorbent cartridge system of claim 1.

14. The method of claim 13, wherein the dialysis fluid is passed through the sorbent cartridge system for a treatment session having a duration of 180 minutes to 300 minutes, wherein the dialysis fluid flows concurrently through the first region at a first fluid flow rate and through the second region at a second fluid flow rate, wherein the first fluid flow rate is at least 5% more than the second fluid flow rate for at least 90% of the treatment session.

15. The method of claim 13, wherein the dialysis fluid is passed through the sorbent cartridge system for a treatment session having a duration of 180 minutes to 300 minutes, wherein the dialysis fluid flows concurrently through the first region at a first fluid flow rate and through the second region at a second fluid flow rate, wherein the first fluid flow rate is at least 10% more than the second fluid flow rate for 100% of the treatment session.

16. The method of claim 13, wherein the dialysis fluid is passed through the sorbent cartridge system for a treatment session having a duration of 180 minutes to 300 minutes, wherein the dialysis fluid flows concurrently through the first region at a first fluid flow rate and through the second region at a second fluid flow rate, wherein the first fluid flow rate is at least 15% more than the second fluid flow rate for at least 90% of the treatment session.

17. A dialysis system to regenerate or purify spent dialysis fluid comprising the sorbent cartridge system of claim 1.

* * * * *